(12) United States Patent
Mogi et al.

(10) Patent No.: US 12,023,453 B2
(45) Date of Patent: Jul. 2, 2024

(54) ASSISTIVE JET ASPIRATION THROMBECTOMY CATHETER AND METHOD OF USING SAME

(71) Applicant: ASAHI INTECC CO., LTD., Seto (JP)

(72) Inventors: Takeshi Mogi, Irvine, CA (US); Michael K. Luk, Lake Forest, CA (US); Satoshi Namima, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 0 days.

(21) Appl. No.: 17/392,646

(22) Filed: Aug. 3, 2021

(65) Prior Publication Data

US 2021/0361305 A1 Nov. 25, 2021

Related U.S. Application Data

(62) Division of application No. 15/987,583, filed on May 23, 2018, now abandoned.
(Continued)

(51) Int. Cl.
*A61M 25/00* (2006.01)
*A61B 17/22* (2006.01)
*A61B 17/3203* (2006.01)

(52) U.S. Cl.
CPC .......... *A61M 25/007* (2013.01); *A61B 17/22* (2013.01); *A61M 25/0071* (2013.01);
(Continued)

(58) Field of Classification Search
CPC .......... A61B 17/22; A61B 2017/22038; A61B 17/3203; A61B 17/32037;
(Continued)

(56) References Cited

U.S. PATENT DOCUMENTS

| 4,368,730 A | 1/1983 | Sharrock |
| 5,603,703 A | 2/1997 | Elsberry et al. |

(Continued)

FOREIGN PATENT DOCUMENTS

| EP | 0 485 133 A1 | 5/1992 |
| EP | 1 092 396 A2 | 4/2001 |

(Continued)

OTHER PUBLICATIONS

Nov. 8, 2018 International Search Report issued in Application No. PCT/IB2018/000783.
(Continued)

*Primary Examiner* — Kami A Bosworth
*Assistant Examiner* — Avery Smale
(74) *Attorney, Agent, or Firm* — Oliff PLC

(57) ABSTRACT

Embodiments disclosed herein relate to an aspiration catheter comprising a catheter body that can have a first end and a second end and an aspiration lumen extending through the catheter body. The aspiration lumen can have an aspiration opening located in a distal portion of the aspiration catheter. The catheter can have an assistive jet element extending through a wall of the aspiration lumen. The assistive jet element can have an assistive jet channel. The assistive jet element can be adaptable to draw blood through the assistive jet element from a location outside of the catheter body adjacent to the assistive jet element and into the aspiration lumen when suction is applied to the aspiration lumen and can be configured to break apart a thrombus or obstruction in the aspiration lumen.

6 Claims, 16 Drawing Sheets

Related U.S. Application Data

(60) Provisional application No. 62/510,193, filed on May 23, 2017.

(52) U.S. Cl.
CPC ............. *A61B 2017/22038* (2013.01); *A61B 2017/22079* (2013.01); *A61B 2017/22084* (2013.01); *A61B 17/32037* (2013.01); *A61B 2217/005* (2013.01); *A61M 2025/0037* (2013.01); *A61M 25/0074* (2013.01); *A61M 2025/0098* (2013.01); *A61M 2206/20* (2013.01)

(58) Field of Classification Search
CPC ........... A61B 2017/22079; A61B 2017/22084; A61B 2217/005; A61M 2025/0098; A61M 25/0068; A61M 25/007; A61M 2206/20; A61M 25/0026; A61M 25/003; A61M 2025/0037; A61M 25/0067; A61M 25/0071; A61M 2025/0073; A61M 25/00; A61M 25/0021; A61M 25/0023; A61M 25/0029; A61M 2025/0031; A61M 2025/004; A61M 25/0043; A61M 25/0082; A61M 1/71; A61M 1/74; A61M 1/84; A61M 1/87
See application file for complete search history.

(56) References Cited

U.S. PATENT DOCUMENTS

| | | | |
|---|---|---|---|
| 5,827,229 | A | 10/1998 | Auth et al. |
| 6,589,227 | B2 | 7/2003 | Klint |
| 6,719,718 | B2 | 4/2004 | Bonnette et al. |
| 6,849,068 | B1 | 2/2005 | Bagoisan et al. |
| 6,979,318 | B1 | 12/2005 | McDonald et al. |
| 7,294,117 | B2 | 11/2007 | Provost-tine et al. |
| 7,608,063 | B2 | 10/2009 | Le et al. |
| 7,938,820 | B2 | 5/2011 | Webster et al. |
| 7,942,852 | B2 | 5/2011 | Mas et al. |
| 7,947,012 | B2 | 5/2011 | Spurchise et al. |
| 8,048,032 | B2 | 11/2011 | Root et al. |
| 8,133,214 | B2 | 3/2012 | Hayase et al. |
| 8,409,237 | B2 | 4/2013 | Galdonik et al. |
| 8,430,837 | B2 | 4/2013 | Jenson et al. |
| 8,721,625 | B2 | 5/2014 | Klint |
| 8,771,289 | B2 | 7/2014 | Mohiuddin et al. |
| 8,814,890 | B2 | 8/2014 | Miyata et al. |
| 8,900,179 | B2 | 12/2014 | Jenson et al. |
| 8,920,402 | B2 | 12/2014 | Nash et al. |
| 9,060,895 | B2 | 6/2015 | Hartley et al. |
| 9,248,221 | B2 | 2/2016 | Look et al. |
| 9,282,992 | B2 | 3/2016 | Levine et al. |
| 9,433,427 | B2 | 9/2016 | Look et al. |
| 9,510,854 | B2 | 12/2016 | Mallaby |
| 9,883,877 | B2 | 2/2018 | Look et al. |
| 2002/0035347 | A1* | 3/2002 | Bagaoisan ......... A61M 25/1011 604/35 |
| 2002/0177800 | A1 | 11/2002 | Bagaoisan et al. |
| 2002/0188167 | A1 | 12/2002 | Viole et al. |
| 2004/0049225 | A1 | 3/2004 | Denison |
| 2005/0277976 | A1 | 12/2005 | Galdonik et al. |
| 2006/0004325 | A1 | 1/2006 | Hamatake et al. |
| 2006/0122575 | A1 | 6/2006 | Nakabayashi |
| 2006/0129091 | A1* | 6/2006 | Bonnette ................ A61B 17/22 604/93.01 |
| 2006/0189921 | A1 | 8/2006 | Galdonik et al. |
| 2007/0060908 | A1 | 3/2007 | Webster et al. |
| 2007/0060944 | A1 | 3/2007 | Boldenow et al. |
| 2007/0106211 | A1 | 5/2007 | Provost-Tine et al. |
| 2007/0191812 | A1 | 8/2007 | Nishide et al. |
| 2007/0270767 | A1* | 11/2007 | Khieu ............... A61M 25/0068 604/35 |
| 2008/0243153 | A1* | 10/2008 | Nguyen ........... A61B 17/32037 606/159 |
| 2010/0094201 | A1 | 4/2010 | Mallaby |
| 2010/0204712 | A1 | 8/2010 | Mallaby |
| 2012/0071838 | A1 | 3/2012 | Fojtik |
| 2013/0178790 | A1 | 7/2013 | Tekulve |
| 2013/0268048 | A1 | 10/2013 | Watson et al. |
| 2015/0327875 | A1 | 11/2015 | Look et al. |
| 2016/0113676 | A1 | 4/2016 | Tada et al. |
| 2016/0166266 | A1 | 6/2016 | Nita |
| 2017/0043137 | A1 | 2/2017 | Felkins et al. |
| 2017/0065396 | A1 | 3/2017 | Look et al. |
| 2017/0216503 | A1 | 8/2017 | Look et al. |

FOREIGN PATENT DOCUMENTS

| | | |
|---|---|---|
| EP | 2138200 A1 | 12/2009 |
| EP | 2138200 B1 | 2/2013 |
| JP | 2008-515463 A | 5/2008 |
| JP | 2013-514869 A | 5/2013 |
| WO | 98/38929 A1 | 9/1998 |
| WO | 2002/083229 A2 | 10/2002 |
| WO | 2014/147815 A1 | 9/2014 |

OTHER PUBLICATIONS

Nov. 8, 2018 Written Opinion of the International Search Authority issued in Application No. PCT/IB2018/000783.

Archived "Pronto extraction catheter", Vascular Solutions, https://web.archive.org/web/20121031024928/http://www.whichmedicaldevice.com:80/by-manufacturer/78/364/pronto-extraction-catheter, originally published on Feb. 2, 2012, and archived by The Wayback Machine on Oct. 31, 2012 (2 pages).

"Pronto V4 Extraction Catheter, New V4 Version", Vascular Solutions, http://vasc.com/pronto-v4/, accessed online May 4, 2018 (1 page). Applicant believes this document and the device described therein was publicly available before the filing date of this application.

* cited by examiner

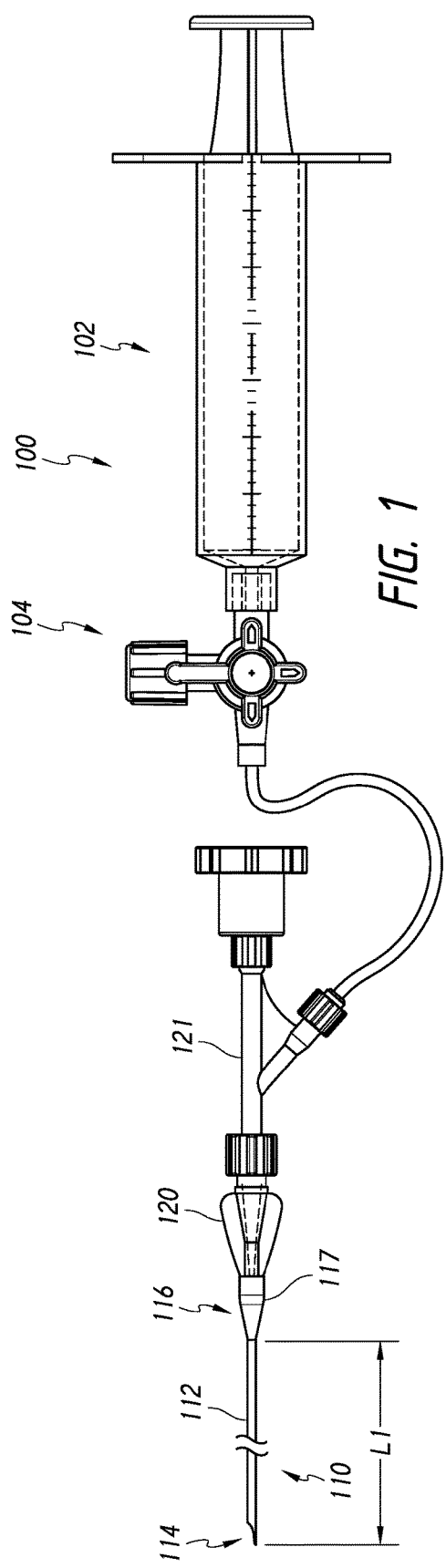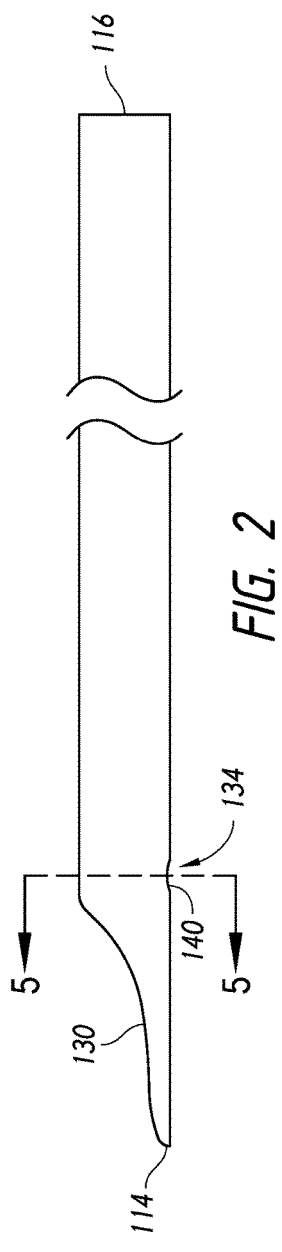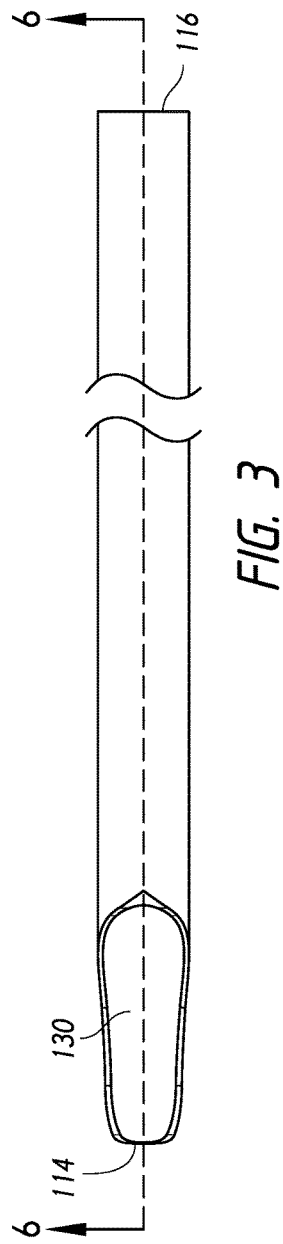

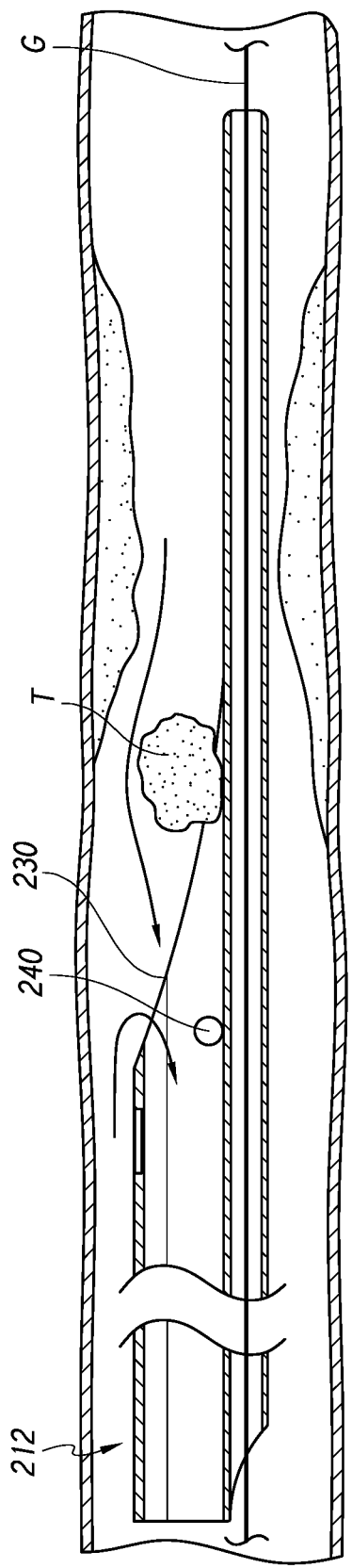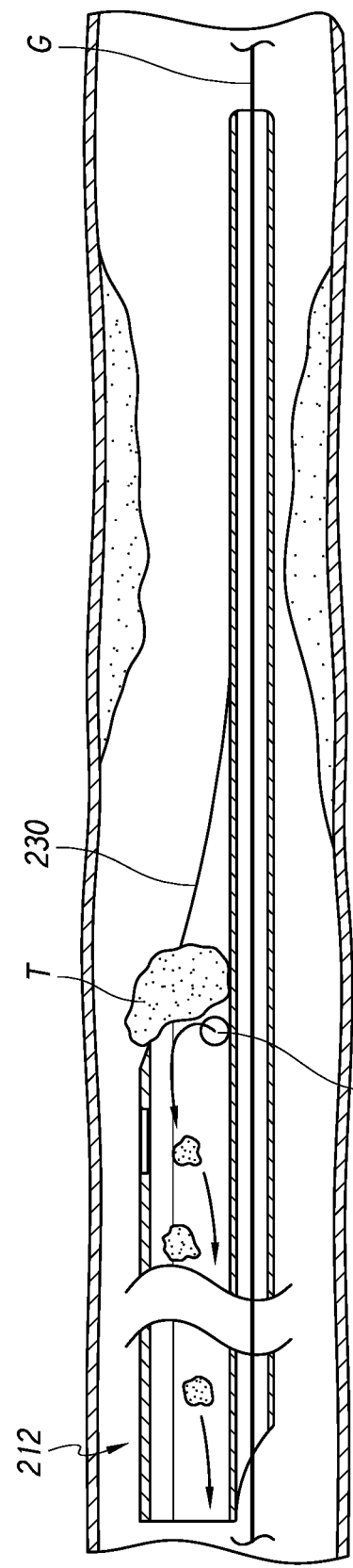

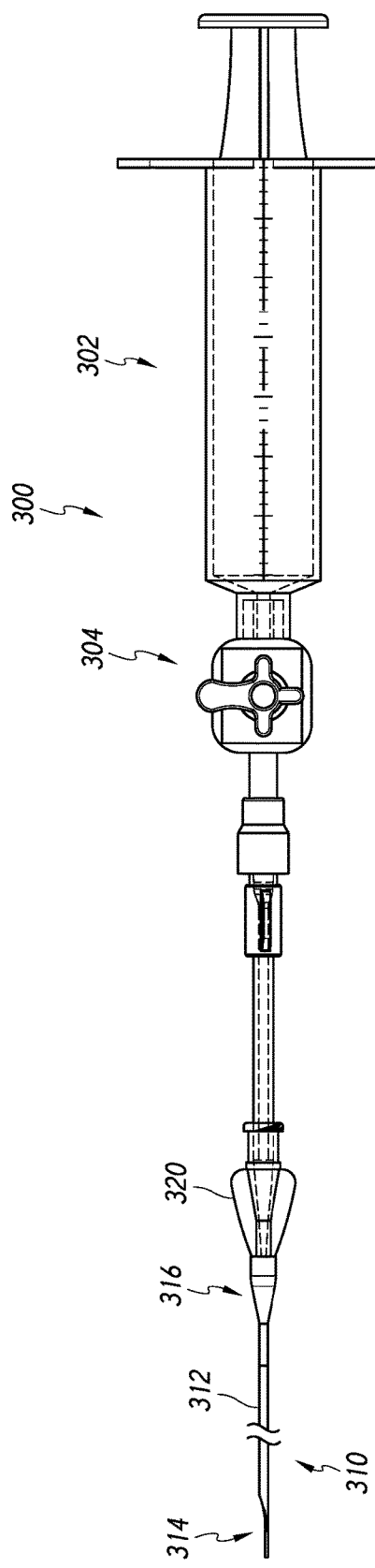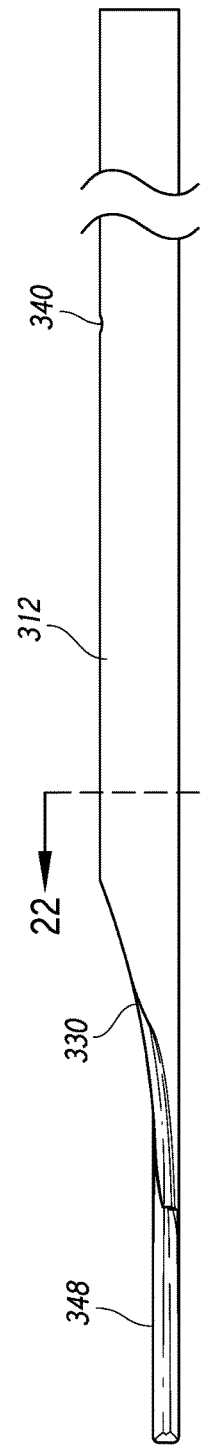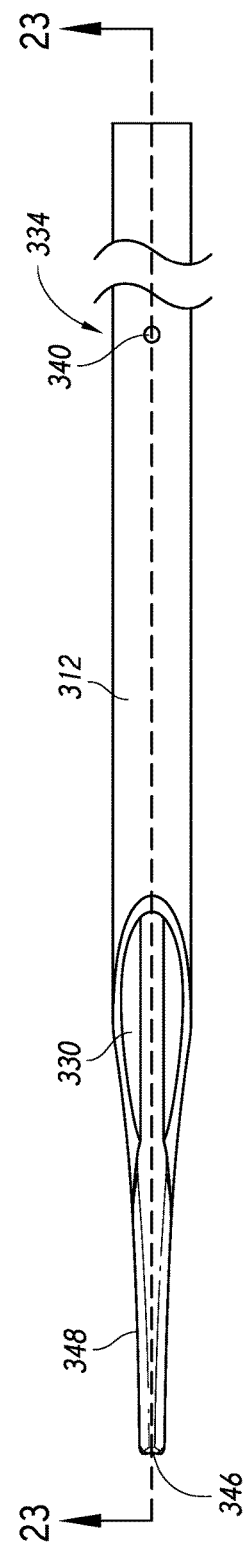
FIG. 18
FIG. 19
FIG. 20

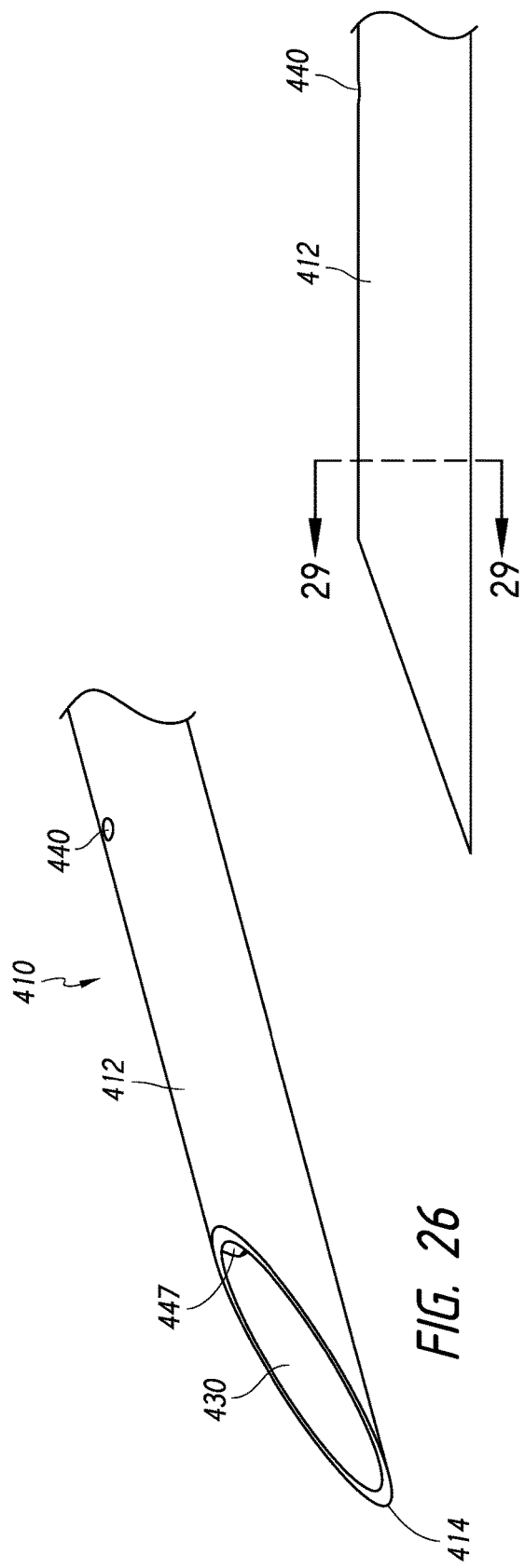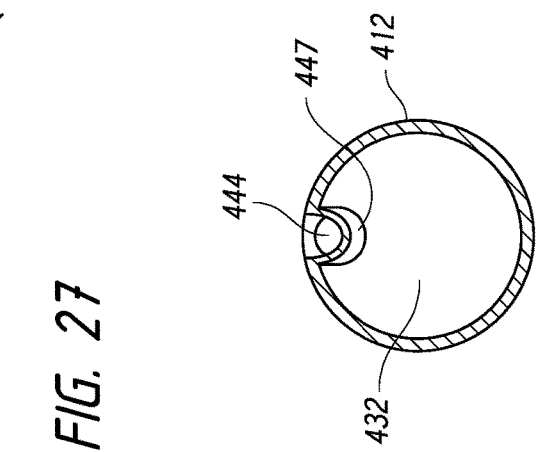
FIG. 26
FIG. 27
FIG. 28
FIG. 29

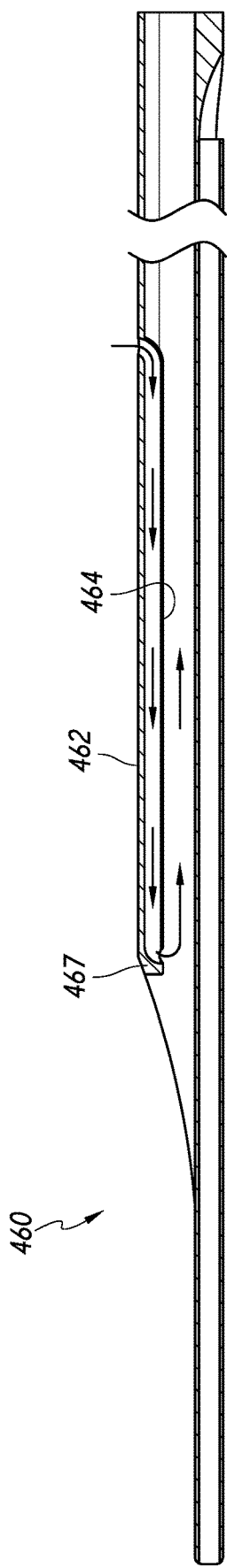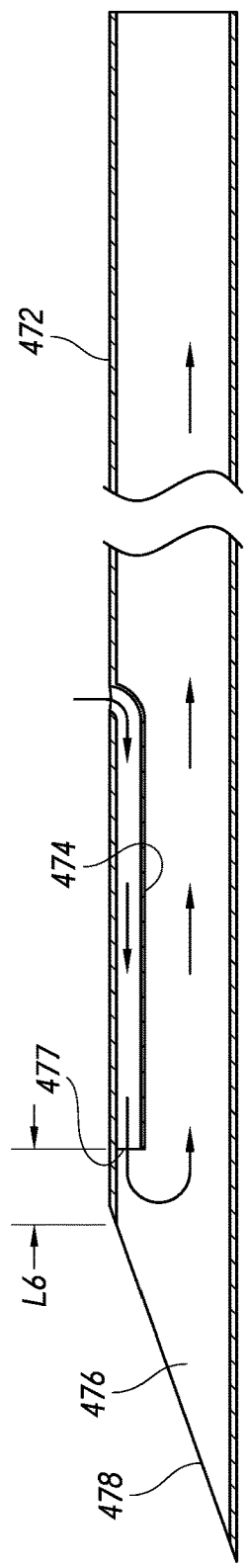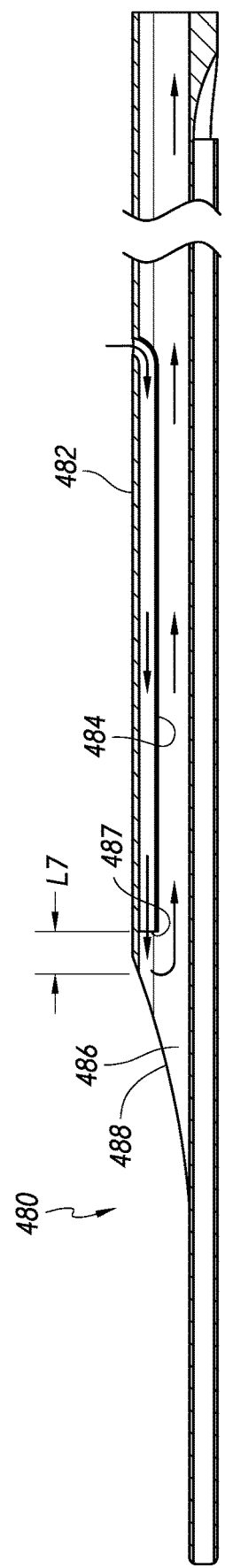

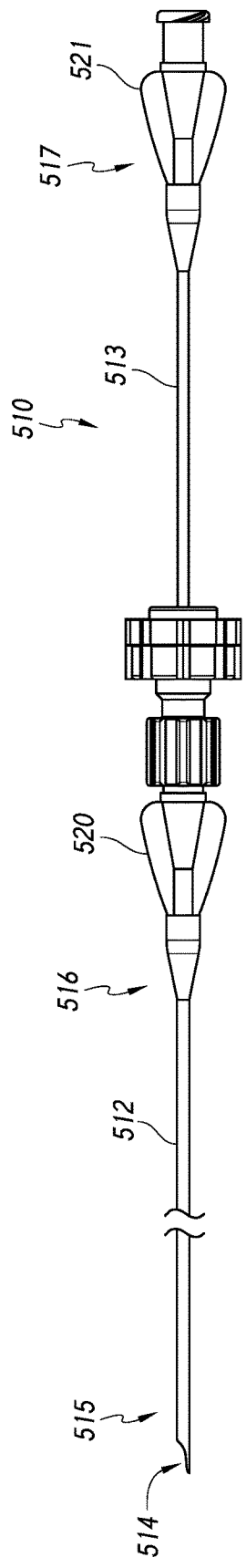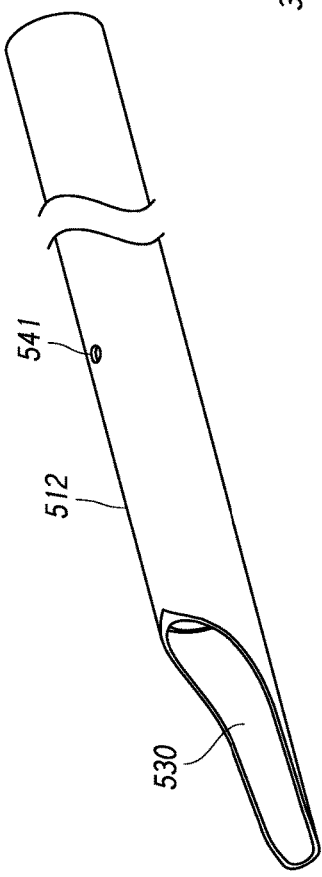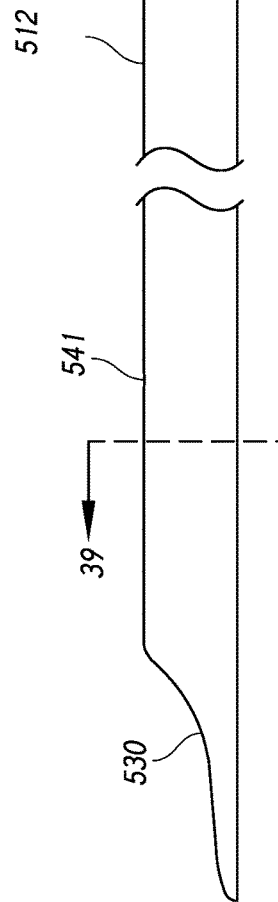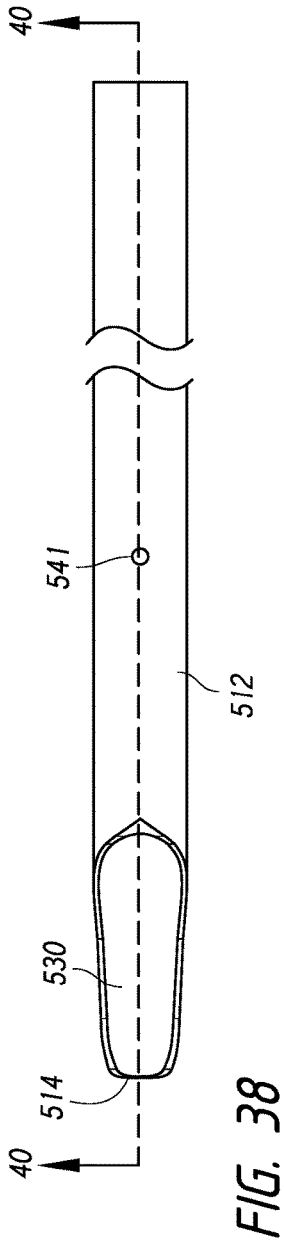
FIG. 35
FIG. 36
FIG. 37
FIG. 38

ASSISTIVE JET ASPIRATION THROMBECTOMY CATHETER AND METHOD OF USING SAME

PRIORITY CLAIM

The present application is a divisional application of U.S. Ser. No. 15/987,583, filed May 23, 2018, which in turn claims priority from U.S. Patent Application No. 62/510,193, filed on May 23, 2017, titled ASSISTIVE JET ASPIRATION THROMBECTOMY CATHETER AND METHOD OF USING SAME, the content of which is incorporated by reference herein in its entirety. The benefit of priority is claimed under the appropriate legal basis including, without limitation, under 35 U.S.C. § 119(e).

BACKGROUND OF THE DISCLOSURE

Field of the Disclosure

The disclosure relates to aspiration catheters, in particular, to aspiration catheters that have an assistive jet element to improve aspiration of thrombus and/or emboli.

Background and Description of the Related Art

A thrombus, which is also referred to as a blood clot, can adhere to the wall of a blood vessel and can obstruct blood flow through healthy blood vessels. An Acute Myocardial Infarction ("AMI") is an example of an extreme condition that can obstruct blood flow. Thrombus aspiration is a medical procedure used for the treatment of ST-segment-elevation myocardial infarction (STEMI). Thrombectomy refers to a procedure for removal of blood clots from a patient's vasculature.

Aspiration catheters can be used to perform thrombectomy procedures, but present many challenges to medical practitioners and have many limitations to their effectiveness. Conventional aspiration catheters currently available on the market have focused mainly on overcoming certain design challenges such as kinking, aspiration power in terms of flow cross-sectional area and deliverability. However, currently available aspiration catheters have not been able to provide an adequate solution to one of the most critical challenges of the first generation catheters, which is, clogging by thrombus, including high consistency thrombus. Conventional aspiration catheters are susceptible to clogging at the aspiration opening with thrombus that the surgeon intends to remove. In many cases, the thrombus is larger than the diameter of the aspiration lumen, leading to such clogging. High consistency thrombus can present a greater risk of clogging to aspiration catheters. Additionally, physicians may prefer to use 6F (6 French) and 7F (7 French) guide compatible aspiration catheters for some patients. This generally small size can result in limited suction power and an increased risk of becoming clogged with thrombus or other debris or objects.

When aspiration is activated using a conventional aspiration catheter, when the blockage in the blood vessel is severe, the flow stream will generally mainly come in from the proximal side of the blockage where the catheter has been advanced toward the blockage from the proximal side of the vessel. In some cases, this will be downstream relative to the distal end of the catheter.

When a large piece or volume of thrombus is drawn toward the aspiration opening of a conventional aspiration catheter, the main flow into the aspiration lumen will come from the proximal side of the aspiration opening because flow from the distal end or side of the aspiration opening will generally be impeded by the thrombus inside the ruptured plaque. The constriction caused by the plaque has a tendency to constrict the flow of blood distal to the end of the aspiration lumen, resulting in a greater flow velocity coming from the blood that is proximal to the distal end of the catheter. Additionally, if the thrombus is large and dense enough to cover and constrict the aspiration opening, a clog in the aspiration catheter can significantly restrict if not terminate all aspiration through the aspiration opening.

Maintaining a flow of fluid from through the aspiration lumen during the aspiration procedure is important to effectively and reliably removing thrombus during an aspiration procedure. Additionally, significantly reducing or eliminating the probability of clogging of the aspiration opening and/or aspiration catheter is also important to effectively and reliably removing thrombus during an aspiration procedure. In other words, it is also important to reduce the risk of a blockage of the aspiration lumen by thrombus plugging up the aspiration lumen, which will result in a significant if not complete stoppage of fluid flow through the aspiration lumen.

The negative impacts of a clogged aspiration catheter go beyond the effectiveness of the aspiration procedure alone. A clogged aspiration catheter can have other significant medical impacts or present significant medical risks to the patient. When a catheter is clogged, a physician would typically retract the aspiration catheter out from the guide catheter to gain access to the clogged portion (i.e. aspiration opening) of the aspiration catheter to remove the clog from the aspiration catheter. This step is not only inconvenient, but, can also generate emboli and eventually lead to ischemic stroke. Emboli can be generated when the clogged thrombus at the distal opening of the aspiration catheter gets sheared off by the tip of the guide catheter when passes through. If the thrombus is only partially aspirated by the aspiration catheter due to a clog in the catheter, the remaining portion (i.e., a portion of the thrombus not in the aspiration) of the thrombus can be sheared by the catheter and/or can generate an emboli. The thrombus embolus can migrate toward the brain and can cause ischemic stroke and/or other complications. An aspiration catheter that has a lower risk of being clogged will reduce the overall risk of the procedure to the patient.

Using conventional aspiration catheters, physicians may not know best the way to clear a clogged catheter as their attention is typically directed to the monitor and not the catheter or syringe. A physician may not even realize that the catheter system has become clogged. Therefore, the physician may not realize that they are not effectively aspirating thrombus. By reducing the risk of clogging during aspiration, physicians would spend more time removing thrombus during the procedure. Additionally, eliminating the time consuming and risky process of clearing a clogged aspiration lumen would also make the procedure more time efficient and safer for the patients.

Some currently available aspiration catheters have additional mechanisms or components such as an active saline jet that can direct a stream of saline fluid from an external source at the thrombus. But, such additional components or mechanisms, such as the saline power flow components, can add significant complexity to such systems and complications to aspiration procedures. Additionally, such additional components or mechanisms can negatively affect the flexibility and deliverability of the catheter. Active flow systems can have stiffer lumen or catheter bodies, that can reduce the overall flexibility of the catheter system. For example, conventional active flow systems can have a stiff tube or lumen for the supply of a saline flow, making the catheter less flexible and potentially less suitable for tortuous anatomy.

The addition of such mechanisms or components can also increase the cost of the system, which can also have a significant impact on the acceptability or feasibility of the catheter system.

Additionally, some doctors currently use a pecking motion technique to remove the thrombus, which is pushing and pulling the catheter in and out repeatedly during the aspiration of thrombus. This motion can help to prevent the catheter from clogging and also to help to break up the thrombus. This technique can lead to operator variations because it is difficult for different doctors to perform this technique the same way, following the same rate of movement, same displacement, etc. With the improved aspiration catheters disclosed herein, doctors will be less likely to rely on or use the pecking motion technique since the embodiments disclosed herein present a significantly lower risk of clogging, if not completely eliminate the risk of clogging. Reducing this operator variation by providing an aspiration catheter that is effective for removing thrombus at a reduced clog risk, i.e., using the embodiments of the improved, can thereby improve the consistency and potentially the effectiveness of aspiration thrombectomy procedures.

Embodiments of the assistive jet catheter systems presented herein reduce the instance or risk of the aspiration lumen of such systems from clogging during use. Therefore, the aspiration catheter embodiments presented herein can significantly improve patient safety and aspiration effectiveness, as will be described below.

SUMMARY OF SOME EMBODIMENTS

The systems, methods and devices described herein have innovative aspects, no single one of which is indispensable or solely responsible for their desirable attributes. Without limiting the scope of the claims, some of the advantageous features will now be summarized.

Some embodiments of the present disclosure are directed to an aspiration catheter adapted to automatically remove and/or aspirate any clogs in the aspiration lumen. As such, some embodiments of the catheter are configured such that the catheter will not get clogged, or will be significantly less likely to get clogged than conventional aspiration catheters, when used in aspiration procedures. Aspiration procedures include, but are not limited to, procedures for ST-Elevation Myocardial Infarction (STEMI) patients. However, any embodiments disclosed herein can be configured to remove thrombus or clots in any suitable area of the body, including but not limited to any coronary, neurovascular, pulmonary, venous, and peripheral applications or areas of the body. Some embodiments disclosed herein are directed to a new generation of aspiration catheter that has a feature called "assistive jet" on the distal end, which can help to unclog an aspiration lumen blocked by thrombus.

Any of the embodiments disclosed herein can have any of the, or any combination of any of the components, features, or details of any of the following arrangements.

Arrangement 1: An assistive jet aspiration catheter comprising:
 a catheter body having a distal end, a proximal end, and an outer wall;
 an aspiration lumen extending through the catheter body along an axial length of the catheter body from the distal end of the catheter body to the proximal end of the catheter body;
 a distal tip positioned at the distal end of the catheter body, the distal tip having an aspiration opening in communication with the aspiration lumen; and
 an assistive jet element comprising an assistive jet inlet opening extending through the outer wall in the catheter body and in communication with the aspiration lumen;
 wherein the assistive jet element can be adaptable to draw fluid (which can be, without limitation, blood and/or other fluid such as saline) through the assistive jet inlet opening from a location outside of the aspiration lumen and to direct an assistive jet flow of fluid toward a blockage in the aspiration lumen distal to the assistive jet inlet opening when suction is applied to the aspiration lumen and when the aspiration lumen is partially or fully blocked by the blockage distal to the assistive jet opening.

Arrangement 2: The aspiration catheter of Arrangement 1, wherein an axial centerline of the assistive jet inlet opening can be positioned from approximately 2 mm to approximately 10 mm from a proximal edge of the aspiration opening, in a proximal direction.

Arrangement 3: The aspiration catheter of any of the previous Arrangements, wherein the assistive jet element can be sized and configured to draw less than approximately 20% (or, approximately 10%) by volume of the total flow aspirated through the aspiration lumen when a flow through the aspiration window is not substantially impeded by blockage.

Arrangement 4: The aspiration catheter of any of the previous Arrangements, wherein the assistive jet element can be sized and configured to draw less than approximately 10% by volume of the total flow aspirated through the aspiration lumen when a flow through the aspiration window is not substantially impeded by blockage.

Arrangement 5: The aspiration catheter of any of the previous Arrangements, wherein the assistive jet element comprises a channel in communication with the assistive jet inlet opening, the channel providing an enclosed lumen extending from the assistive jet inlet opening to an assistive jet outlet opening at a distal end of the enclosed lumen.

Arrangement 6: The aspiration catheter of Arrangement 5, wherein an axial centerline of the assistive jet inlet opening can be positioned between approximately 5 mm and approximately 50 mm from a proximal edge of the aspiration opening.

Arrangement 7: The aspiration catheter of Arrangement 5, wherein the assistive jet outlet opening can be positioned between approximately 5 mm distal to a proximal edge of the aspiration opening to approximately 5 mm proximal to the proximal edge of the aspiration opening Arrangement 8: The aspiration catheter of any of the previous Arrangements, wherein the assistive jet element can be positioned adjacent to the aspiration opening.

Arrangement 9: The aspiration catheter of any of the previous Arrangements, wherein the catheter body comprises a guidewire lumen extending at least from the distal end of the catheter body along a portion of a length of the catheter body.

Arrangement 10: The aspiration catheter of any of the previous Arrangements, wherein a distal end of the guidewire lumen can be distal to the aspiration opening.

Arrangement 11: The aspiration catheter of any of the previous Arrangements, wherein the aspiration opening can be angled in a lengthwise direction of the catheter body.

Arrangement 12: The aspiration catheter of any of the previous Arrangements, wherein the aspiration catheter is a 3 French, 4 French, or 5 French sized catheter, and the assistive jet inlet opening has a cross-sectional size or area that can be from approximately 20% to approximately 50% of a cross-sectional size or area of the aspiration lumen.

Arrangement 13: The aspiration catheter of any of the previous Arrangements, wherein the aspiration catheter is a 6 French or larger sized catheter, and the assistive jet inlet opening has a cross-sectional size that can be from approximately 10% to approximately 40% of a cross-sectional area of the aspiration lumen.

Arrangement 14: An aspiration kit, comprising the aspiration catheter of any of the previous Arrangements and a syringe, the syringe being in communication with the aspiration lumen and providing a source of suction to the aspiration lumen.

Arrangement 15: An assistive jet aspiration catheter comprising:
- a catheter body having a distal end, a proximal end, and an outer wall;
- an aspiration lumen extending through the catheter body along an axial length of the catheter body from the distal end of the catheter body to the proximal end of the catheter body;
- a distal tip positioned at the distal end of the catheter body, the distal tip having an aspiration opening in communication with the aspiration lumen; and
- an assistive jet inlet opening extending through the outer wall in the catheter body and in communication with an assistive jet channel positioned inside the aspiration lumen, the assistive jet channel extending distally from the assistive jet inlet opening to an assistive jet outlet opening;
- wherein:
  - when the aspiration lumen is partially or fully blocked by a thrombus or other mass in the aspiration lumen distal to the assistive jet outlet opening and when suction is applied to a proximal end of the aspiration lumen, the assistive jet aspiration catheter can be configured to draw fluid (which can be, without limitation, blood and/or other fluid such as saline) through the assistive jet inlet opening from a location outside of the aspiration lumen and direct a flow of fluid through the assistive jet channel and toward the blockage in the aspiration lumen; and
  - the assistive jet aspiration catheter can be configured such that such flow of fluid through the assistive jet channel will erode or break apart the thrombus or other mass that is blocking the aspiration lumen.

Arrangement 16: The aspiration catheter of Arrangement 15, wherein the assistive jet element can be sized and configured to draw less than 20% by volume of the total flow aspirated through the aspiration lumen when the aspiration window is not blocked.

Arrangement 17: The aspiration catheter of any one of Arrangements 15-16, wherein the assistive jet inlet opening can be positioned between approximately 5 mm and approximately 50 mm from a proximal edge of the aspiration opening.

Arrangement 18: The aspiration catheter of any one of Arrangements 15-17, wherein the assistive jet outlet opening can be positioned between approximately 5 mm distal to a proximal edge of the aspiration opening to approximately 10 mm proximal to the proximal edge of the aspiration opening.

Arrangement 19: The aspiration catheter of any one of Arrangements 15-18, wherein the catheter body comprises a guidewire lumen extending at least from the distal end of the catheter body along a portion of a length of the catheter body.

Arrangement 20: The aspiration catheter of Arrangement 19, wherein a distal end of the guidewire lumen can be distal to the aspiration opening.

Arrangement 21: The aspiration catheter of any one of Arrangements 15-20, wherein the aspiration opening can be angled in a lengthwise direction of the catheter body.

Arrangement 22: An aspiration kit, comprising the aspiration catheter of any one of Arrangements 15-121 and a syringe, the syringe being in communication with the aspiration lumen and providing a source of suction to the aspiration lumen.

Arrangement 23: An aspiration catheter comprising:
- an inner catheter body having a distal end, a proximal end, and an outer wall having an inside surface and an outside surface;
- an outer catheter body having a distal end, a proximal end, and an outer wall having an inside surface and an outside surface, the outer catheter body being configured to slidably receive the inner catheter body therein such that the outside surface of the outer wall of the inner catheter body is positioned adjacent to the inside surface of the outer wall of the outer catheter body;
- an aspiration lumen extending through the inner catheter body along an axial length of the inner catheter body from the distal end of the inner catheter body to the proximal end of the inner catheter body;
- a distal tip positioned at the distal end of the catheter body, the distal tip having an aspiration opening in communication with the aspiration lumen;
- wherein:
  - the aspiration catheter has an inner opening extending through the outer wall of the inner catheter and an outer opening extending through the outer wall of the outer catheter;
  - the inner catheter body can be movable relative to the outer catheter body between at least a first position in which the inner and outer openings are at least substantially in alignment with one another and a second position in which the inner and outer openings are out of alignment with one another such that the inner opening of the inner catheter is at least substantially covered by the outer wall of the outer catheter;
  - when the inner catheter body is in the first position, when suction is applied to the catheter, and when a portion of the aspiration lumen distal to the inner opening in the inner catheter body is at least partially obstructed by an obstruction, the catheter will draw a flow fluid from outside of the outer catheter body through the inner and outer openings and into the aspiration lumen; and
  - the aspiration catheter can be configured such that such flow of fluid will assist in the removal of the obstruction.

Arrangement 24: The aspiration catheter of Arrangement 23, wherein an axial centerline of the inner opening can be positioned from approximately 2 mm to approximately 10 mm from a proximal edge of the aspiration opening, in a proximal direction.

Arrangement 25: The aspiration catheter of any one of Arrangements 23-24, wherein the inner opening can be sized and configured to draw less than approximately 20% by volume of the total flow aspirated through the aspiration lumen when a flow through the aspiration window is not substantially impeded by blockage.

Arrangement 26: The aspiration catheter of any one of Arrangements 23-25, wherein the inner opening can be sized and configured to draw less than approximately 10% by volume of the total flow aspirated through the aspiration lumen when a flow through the aspiration window is not substantially impeded by blockage.

Arrangement 27: The aspiration catheter of any one of Arrangements 23-26, wherein the assistive jet element comprises a channel in communication with the inner opening in the inner catheter, the channel providing an enclosed lumen extending from the inner opening to an assistive jet outlet opening at a distal end of the enclosed lumen.

Arrangement 28: The aspiration catheter of Arrangement 27, wherein an axial centerline of the inner opening can be positioned between approximately 5 mm and approximately 50 mm from a proximal edge of the aspiration opening.

Arrangement 29: The aspiration catheter of Arrangement 27, wherein the assistive jet outlet opening can be positioned between approximately 5 mm distal to a proximal edge of the aspiration opening to approximately 5 mm proximal to the proximal edge of the aspiration opening Arrangement 30: The aspiration catheter of any one of Arrangements 23-29, wherein the catheter body comprises a guidewire lumen extending at least from the distal end of the catheter body along a portion of a length of the catheter body.

Arrangement 31: The aspiration catheter of Arrangement 30, wherein a distal end of the guidewire lumen can be distal to the aspiration opening.

Arrangement 32: The aspiration catheter of any one of Arrangements 23-31, wherein the aspiration catheter is a 3 French, 4 French, or 5 French sized catheter, and the inner opening has a cross-sectional area that can be from approximately 20% to approximately 50% of a cross-sectional area of the aspiration lumen.

Arrangement 33: The aspiration catheter of any one of Arrangements 23-32, wherein the aspiration catheter is a 6 French or larger sized catheter, and the inner opening has a cross-sectional area that can be from approximately 10% to approximately 40% of a cross-sectional area of the aspiration lumen.

Arrangement 34: An aspiration kit, comprising the aspiration catheter of any one of Arrangements 23-33 and a syringe, the syringe being in communication with the aspiration lumen and providing a source of suction to the aspiration lumen.

Arrangement 35: A method of aspirating a mass of thrombus from a vessel, comprising:
advancing an aspiration catheter having a catheter body into the vessel;
applying suction to the aspiration catheter;
drawing a flow of fluid through an opening in the catheter body that is positioned adjacent to a distal end of the catheter body;
breaking apart a thrombus positioned adjacent to or in contact with a distal end of the catheter body with the flow of fluid flowing through the opening, causing smaller pieces of thrombus that can be aspirated by the aspiration catheter to break apart.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings. Embodiments of the present disclosure will now be described hereinafter, by way of example only, with reference to the accompanying drawings in which:

FIG. 1 is a side view of an embodiment of an assistive jet aspiration catheter system of an over-the-wire configuration, showing a portion of the catheter in a loop to reduce the size of the figure.

FIG. 2 is a side view of the assistive jet catheter body of the embodiment of the assistive jet aspiration catheter system shown in FIG. 1.

FIG. 3 is a top view of the assistive jet catheter body shown in FIG. 2.

FIG. 16 is a section view of the assistive jet catheter body shown in FIG. 10, illustrating aspiration of a mass of thrombus.

FIG. 17 is a section view of the assistive jet catheter body shown in FIG. 10, illustrating aspiration of a mass of thrombus.

FIG. 18 is a side view of another embodiment of an aspiration catheter system, showing a portion of the catheter in a loop to reduce the size of the figure.

FIG. 19 is a side view of the assistive jet catheter body of the embodiment of the assistive jet aspiration catheter system shown in FIG. 18.

FIG. 20 is a top view of the assistive jet catheter body shown in FIG. 19.

FIG. 26 is a perspective view of another embodiment of an assistive channel aspiration catheter.

FIG. 27 is a side view of the assistive jet catheter body shown in FIG. 26.

FIG. 28 is a top view of the assistive jet catheter body shown in FIG. 26.

FIG. 29 is a section view of the assistive jet catheter body shown in FIG. 19, taken through line 29-29 of FIG. 27.

FIG. 32 is a section view of another embodiment of an assistive channel aspiration catheter.

FIG. 33 is a section view of another embodiment of an assistive channel aspiration catheter.

FIG. 34 is a section view of another embodiment of an assistive channel aspiration catheter.

FIG. 35 is a side view of another embodiment of an assistive jet aspiration catheter, being of an over-the-wire configuration.

FIG. 36 is a perspective view of a distal portion of the aspiration catheter shown in FIG. 35.

FIG. 37 is a side view of a distal portion of the aspiration catheter shown in FIG. 35.

FIG. 38 is a top view of a distal portion of the aspiration catheter shown in FIG. 35.

DETAILED DESCRIPTION

Figure 5:
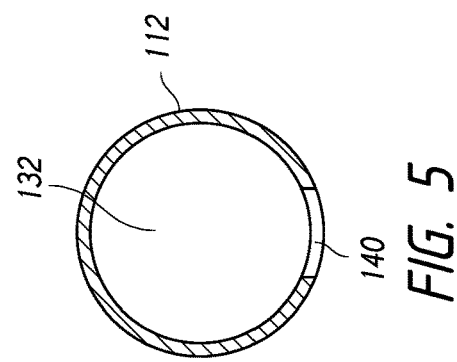
FIG. 5 is a section view of the assistive jet catheter body shown in FIG. 2, taken through line 5-5 of FIG. 2.

Embodiments of systems, components, methods, and details of assembly and manufacture are described herein, with reference to the accompanying figures, wherein like numerals refer to like or similar elements throughout. Although several embodiments, examples, and illustrations are disclosed below, the inventions described herein extend beyond the specifically disclosed embodiments, examples, and illustrations and can include other uses of the inventions and obvious modifications and equivalents thereof, and combinations of any of the embodiments, features, and details of any of the embodiments disclosed herein with other of the embodiments disclosed herein. Additionally, the descriptions of all of the embodiments disclosed herein should be interpreted to include any of the features, components, and other details of any of the other embodiments disclosed here in combination with or in the alternative to any of the features, components, and other details explicitly described herein to form new embodiments, all of which are included as part of this disclosure.

Additionally, the terminology used herein is not intended to be interpreted in any limited or restrictive manner simply because it is being used in conjunction with a detailed description of certain specific embodiments of the inventions. Also, embodiments of the inventions can comprise several novel features and no single feature is solely responsible for its desirable attributes or is essential to practicing the inventions herein described.

Certain terms may be used in the following description for the purpose of reference only, and thus are not intended to be limiting. For example, terms such as "above" and "below" may refer to directions in the drawings to which reference is made or to a direction relative to the orientation of the embodiment in an operable position. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Embodiments presented herein address significant shortcoming or problems of the currently available aspiration catheters, which can include clogging of the aspiration lumen of the catheter by the thrombus that such catheters are designed to remove. As will be discussed, some or all embodiments of the assistive jet catheter systems presented herein produce a range of performance and usability advantages over the presently available aspiration catheters.

Embodiments of the assistive jet catheter systems presented herein are configured to produce a flow of fluid flow from the patient's bloodstream that can be used to break up thrombus within, adjacent to, or near a distal portion of the aspiration lumen. In any embodiments disclosed herein, saline or other suitable fluid can be provided to the patient's vessel near the target area, and the blood, saline, and/or other fluid can be drawn through the assistive jet element to break apart or erode the thrombus. This addition of the assistive jet can reduce the size of the thrombus being aspirated by breaking the thrombus up into smaller pieces or masses, thereby reducing the likelihood of the aspiration lumen becoming clogged. Pieces or masses from the larger thrombus are aspirated through the catheter's aspiration lumen as the larger mass of the thrombus is being reduced in size.

For example, any embodiments of the assistive jet aspiration catheter disclosed herein can have an assistive jet element that can be used to draw blood from the patient's blood vessel and direct the flow of blood from the patient's blood vessel at the thrombus, thereby eroding and/or breaking apart the thrombus. In some embodiments, the assistive jet element or assistive jet elements can comprise any assistive jet channel features or components, assistive jet opening features or components, and/or other features, components, or elements adapted to draw fluid flow (for example, blood) from the patient's vessel and direct said fluid toward the opening of the aspiration catheter. The assistive jet through the assistive jet element can be used to erode or break apart thrombus positioned in contact with or adjacent to the opening of the aspiration catheter.

In any embodiments and without limitation, the assistive jet element can comprise an opening through the catheter body wall positioned near the opening of the aspiration lumen, a separate flow channel having a first or inlet opening in communication with the patient's blood stream outside of the catheter body and a second or outlet opening adjacent to an opening of the aspiration lumen, or any other suitable features or combinations of features configured to direct a flow of blood from the patient's blood stream toward or at the opening of the aspiration lumen. In some embodiments, the opening of the assistive jet element (which can have a channel) can be selectively openable and/or closeable so that a physician can have better control over the operation of the assistive jet element.

In some embodiments, the catheter body can have any combination of assistive jet channel and assistive jet openings (for example, holes) in the catheter body. For example, the catheter body can have as aspiration flow lumen in addition to one or more aspiration flow openings that are positioned in the catheter body distal to the opening of the aspiration flow lumen. Fluid or blood flow through the assistive jet channel can flow through the assistive jet channel in a direction that is opposite to the direction of aspiration, such that the fluid or blood flow through the assistive jet channel can be directed at the thrombus or other debris that is positioned in contact with or adjacent to the aspiration opening. This can increase the effect of the assistive jet in shearing or breaking up the thrombus and, thereafter, removal of the thrombus through the aspiration lumen.

In any embodiments, the opening or channel of the assistive jet element (or any of the assistive jet openings or other assistive jet elements disclosed herein) can be adapted to provide flow from a position that is proximal to the aspiration opening to a position that is adjacent to, just proximal to, distal to a distal edge of an aspiration opening (if the aspiration opening is slanted, etc.) and/or within the aspiration opening. As used herein, the term distal is meant to refer to a position or direction that is closer to the handle portion of the aspiration catheter than the distal dip of the aspiration catheter, When aspiration is activated in the aspiration lumen, flow can come into the aspiration lumen from multiple directions. If not fully obstructed, flow can enter the aspiration lumen through the aspiration lumen opening. Flow can also come through the assistive jet channel and can break up or shear off fragments of any thrombus in the vicinity of the end of the assistive jet channel, so that such fragmented thrombus can be broken up into pieces or sizes that can be aspirated by the aspiration lumen. In any embodiments disclosed herein, though not required, the assistive jet channel or channel can be positioned between the aspiration lumen and a guidewire lumen, if the catheter body has a discrete guidewire lumen. In other embodiments, though not so limited, the assistive jet channel or channel can be positioned on an opposite side of a guidewire lumen as compared to the aspiration lumen.

Any of the assistive jet aspiration catheter embodiments disclosed herein can be configured to work with both rapid exchange and over-the-wire types of catheters. These designs can also be used for catheter with or without guidewire lumen even though most of the catheter applications commonly used today are used with a guidewire. Any embodiments of the assistive jet catheter systems disclosed herein can have a guidewire lumen and a main aspiration lumen that extends from a hub portion at a proximal end of the catheter body to an aspiration opening that can be positioned at a distal end of the catheter body. In any embodiments, the guidewire lumen can extend substantially or completely the entire length of the catheter body, or can extend along only a portion of the catheter body, such as in a rapid exchange configuration. For example, the guidewire lumen can extend through only the distal 15 cm of the catheter body. Any aspiration catheter embodiments disclosed herein can also be designed to not have a guidewire lumen.

Additionally, as mentioned above, any embodiments of the assistive jet catheter systems disclosed herein can have one or more side holes (referred to above as assistive jet openings) near the aspiration opening that can also provide the assistive jet or flow of blood toward the aspiration opening. In some embodiments, a possible advantage of the assistive jet openings relative to aspiration channels is that the assistive jet openings can be more efficient than the aspiration channels. The assistive jet openings can impart a lower pressure loss than the assistive jet channels. This can increase the flow velocity through the aspiration lumen when, for example and without limitation, the flow through the aspiration opening is restricted by thrombus. An advantage of the assistive jet channel, in some embodiments, is that the assistive jet channel can more precisely control the direction of flow of the assistive jet by confining the flow path of the assistive jet since the channel will only permit the flow through the lumen of the channel.

A guide catheter of 7F and 8F size typically has much more suction power and can remove chunks of thrombus much better than a 6F guide catheter or a 6F compatible aspiration catheter. However, 7F and 8F can be too big for some coronary arteries that encounter acute myocardial infarction ("AMI"). 6F or smaller systems are typically the only aspiration catheter systems that can be used in such anatomy. However, at least some conventional 6F aspiration catheters have been shown to be largely ineffective in removing thrombus. The shearing mechanisms of the embodiments of the assistive jet catheter systems presented herein enable the smaller, 6F sized catheters to have the thrombus removing effectiveness of the larger, 7F or 8F aspiration catheters. However, in any embodiments disclosed herein, the assistive jet catheter systems can be used in catheters that are smaller than the 6F size, including but not limited to 4F and 5F sizes, or in catheters that are larger than the 6F size, including 7f or 8F or larger sizes.

Some embodiments of the assistive jet catheter devices disclosed herein can be configured to use flexible catheter bodies, designed to improve the flexibly and/or steerability of the catheter systems. In any embodiments disclosed herein, all or a portion of the catheter body can be rigid and/or formed of metal or other rigid or semi-rigid material. For example, embodiments of the aspiration catheter or device of the present disclosure can be adapted for use to perform biopsy procedures. Such devices can have all or a portion of the catheter body formed from a rigid or semi-rigid material. The embodiments of the assistive jet catheter devices disclosed herein can be suitable for tortuous anatomies. Additionally, any embodiments of the assistive jet catheter devices disclosed herein can utilize catheter bodies with coils, or coil reinforced portions, or braiding. For example, without limitation, the distal portion of the catheter body (the portion closest to the end of the catheter body) can be coil and/or braid reinforced. Embodiments of such systems can have assistive jet components or features integrated into such coil and/or braid reinforced catheter bodies. Additionally, in any embodiments, the catheter body can be coil and/or braid reinforced along all or portions of the catheter body that are proximal to the assistive jet element(s).

Any embodiments of the assistive jet catheter system embodiments disclosed herein can be used to treat a range of conditions, including but not limited to Acute Myocardial Infarction ("AMI"). Any aspiration catheter embodiments disclosed herein can be adapted for use in other parts of the body that may also have a blood clot, such as the leg (deep vein thrombosis), lungs, brain, and/or heart (venous thrombosis). Any aspiration catheter embodiments disclosed herein can be adapted for removing any loose masses that are present in the body, not just within the blood stream.

The assistive jet catheter systems presented herein can be easier to use and require little or no additional training for medical practitioners familiar with known or typical thrombectomy procedures. This can improve the safety and efficiency of the thrombectomy system, and reduce the overall cost of using the embodiments of the assistive jet catheter systems presented herein as compared to more complex, or active flow systems.

Additionally, when conventional aspiration catheters become clogged, all or a portion of the thrombus that is within the aspiration lumen, but which has not yet reached the syringe, will in most cases stop moving toward the syringe since the clogged condition can terminate or significantly reduce the suction pressure. Such clogging can also result in thrombus or other debris positioned within the distal end of the catheter body being emitted from the aspiration lumen back into the patient's vasculature or anatomy, which can present significant risks to the patient.

In contrast, when large and/or high consistency thrombus are drawn into contact with the aspiration opening or aspiration lumen of the assistive jet catheter system embodiments disclosed herein, at least a minimal level of aspiration flow will be maintained in the aspiration lumen due to the fluid flow capabilities of the assistive jet channel or opening, which can provide a fluid flow path that bypasses a clogged portion of the aspiration opening or lumen. Additionally and importantly, this fluid flow from the assistive jet channel or opening can operably shear and/or break up such thrombus, allowing large and/or high consistency thrombus that would clog convention aspiration catheters to be aspirated by the embodiments of the assistive jet catheter systems disclosed herein. This can also prevent thrombus or debris within the aspiration lumen from being ejected into the patient's vasculature, thereby reducing the risk of an embolic condition even when the embodiments of the assistive jet catheter systems become at least partially clogged.

In any embodiments disclosed herein, the assistive fluid flow path can be introduced through an assistive jet channel or lumen that projects in a direction that is parallel with the aspiration lumen. Fluid or blood flow through the assistive jet channel can flow through the assistive jet channel in a direction that is opposite to the direction of aspiration, such that the fluid or blood flow through the assistive jet channel can be directed at the thrombus or other debris that is positioned in contact with or adjacent to the aspiration opening. This can increase the effect of the assistive jet in shearing or breaking up the thrombus.

In any embodiments, the catheter body, aspiration lumen, aspiration opening, and/or assistive jet element(s) can be adapted such that, when suction is applied to the aspiration lumen and there is no obstruction from thrombus or other debris affecting flow through the aspiration lumen, all or substantially all of the fluid flowing into the aspiration lumen will flow through the aspiration opening, with little to no flow through the assistive jet element(s). In this state, the assistive jet element(s) will be effectively disabled unless an obstruction is presented to the aspiration lumen opening. In some embodiments, the assistive jet element can be configured such that, as a thrombus or other mass moves closer to the aspiration opening, the proximity of the thrombus to the aspiration opening can cause the flow of blood through the aspiration opening to be impeded, which obstruction to the flow through the aspiration lumen opening can "activate" the assistive jet element to direct fluid flow toward the aspiration lumen opening.

In these configurations, when suction is applied through the aspiration lumen wherein the aspiration lumen is open (i.e. not impeded or clogged), all or substantially all of the flow of blood, thrombus, and other debris will advance through the aspiration opening and not through the assistive jet element. The assistive jet element will essentially be disabled in this situation.

Additionally, in any embodiments disclosed herein, the assistive fluid flow path can be introduced through an assistive jet opening that is positioned in a distal region of the aspiration catheter. For example and without limitation, the assistive jet opening can be positioned in a side wall of the catheter body or aspiration opening. The assistive jet opening can be a round opening, an ovular opening, or any other suitably shaped opening formed radially through a wall of the catheter body.

Any embodiments can have a single assistive flow inlet opening or multiple assistive jet inlet openings formed in the catheter body. In some embodiments, the single opening can be positioned at any desired radial position, for example, near a bottom portion of the catheter body, near the lateral sides of the catheter body, near the top of the catheter body, or otherwise. For orientation purposes, when the aspiration lumen opening is angled, beveled, or otherwise elongated, the distalmost portion of the aspiration lumen can be at the bottom of the catheter body such that an assistive jet opening positioned at a top of the catheter body can be positioned radially opposite to the distalmost portion of the aspiration lumen. The bottom of the lumen in this orientation can be designated the 6 o'clock position, and the top can be designated the 12 o'clock position. In any embodiments, the assistive jet element inlet element or opening can be positioned approximately at the 7 o'clock position, the 3 and/or 9 o'clock position(s), the 12 o'clock position, or any combination of these positions or therebetween. In embodiments having multiple assistive jet elements, the assistive jet element inlet openings can be positioned approximately at any combination of the 7 o'clock position, the 3 and/or 9 o'clock position, the 12 o'clock position, or any combination of these positions or therebetween, for example, a first assistive jet opening can be positioned at an approximately 12 o'clock position. A second and a third assistive jet opening can be positioned approximately between a 5 o'clock and a 6 o'clock position, and between a 6 o'clock and a 7 o'clock position, respectively. Some embodiments can have two assistive jet elements, a first assistive jet element or opening can be positioned between a 5 o'clock and a 6 o'clock position and a second assistive jet element or opening can be positioned approximately between a 6 o'clock and a 7 o'clock position, respectively.

In any assistive jet aspiration catheter embodiments disclosed herein, the assistive jet openings can be configured to direct the assistive jet in any desired directions, including in different directions. For example, in an embodiment having two assistive jet openings, a first assistive jet opening can direct the flow in a proximal direction (i.e., toward a proximal end of the catheter). A second assistive jet opening can direct the flow in a radially inward direction, or a distal direction.

A deflective or flow direction element can be positioned inside the aspiration lumen, adjacent to the assistive jet element opening, to direct the assistive jet through the lumen toward the aspiration opening, such that the assistive jet can be directed toward thrombus adjacent to or in contact with the aspiration opening. In any embodiments, the deflective or flow direction element can be a tab or protrusion that projects away from the inside surface of the aspiration lumen a short distance, positioned at an adjacent and or side of the assistive jet opening. The deflective or flow direction element can be positioned at an angle or can have a curved surface so as to not significantly disturb the velocity of the assistive jet through the assistive jet opening.

Additionally, any assistive jet aspiration catheter embodiment disclosed herein can have multiple assistive jet openings, each of the assistive jet openings having a different cross-sectional size or diameter. For example, a first assistive jet opening can have a first cross-sectional size or diameter. A second assistive jet opening can have a second cross-sectional size or diameter, the second cross-sectional size or diameter being greater than, less than, or equal to the first cross-sectional size or diameter. Additionally, the assistive jet aspiration catheter embodiment could have a third assistive jet opening, the assistive jet opening having a third cross-sectional size or diameter that is greater than, equal to, or less than the cross-sectional size or diameter of the first and/or second cross-sectional size or diameter.

In any embodiments disclosed herein, the assistive jet opening or the distal opening of the assistive jet channel can be positioned adjacent to the aspiration opening. In any embodiments, including without limitation those where the aspiration opening is slanted, the assistive jet opening or the distal opening of the assistive jet channel can be positioned adjacent to a top portion or a lower portion of the aspiration opening, the top portion being positioned further proximal of the distal end of the aspiration catheter as compared to the lower portion of the aspiration opening, one or both sides of the catheter body, or in any other desired location.

In any embodiments disclosed herein, the assistive jet channels can be small and may possibly be plugged up by the red blood cells flowing through the assistive jet channels. Therefore, the assistive jet openings and channels should be large enough for blood to flow therethrough without restriction. Additionally, in any embodiments, any channels or lumen within the aspiration catheter, including the assistive jet channels and the aspiration lumen, can be coated with PTFE, silicone or similar coating to reduce the likelihood of adhesion of the blood and platelet to the surface of the lumen that can slow down the flow through the lumen. Coating can present a risk of peeling off and impeding flow through the lumen, as well as reducing the flow area through the lumen. Several new materials that have been developed involve either having additive in the polymer itself or treating the surface of the polymer. Examples of such additive modified materials include Interface Biologics's Bio Flo (or Endexo) and Wyss Institute's Tethered-Liquid Perfluorocarbon surface treatment. Any of these materials can be used to coat any of the lumen in any of the embodiments disclosed herein.

With coronary plaque, the size of lesions typically range from 3 mm to 3 cm. The aspiration catheter will usually be pushed through the entire lesion length to remove the thrombus inside the ruptured plaque. It may be useful that the assistive jet inlet opening is located outside of the lesion during this use. On the other hand, the location of these lesion can be from 5 cm to 15 cm deep into the coronary arteries and ideally be outside of the guide catheter when these locations are reached. In any embodiments disclosed herein, the inlet opening for the assistive jet element can be from approximately 6 to approximately 7 cm from the distal edge of the aspiration opening, or from approximately 4 to approximately 5 cm from the distal edge of the aspiration opening. In some embodiments, the length of the aspiration opening and the tip can be from approximately 5 mm to approximately 12 mm long, and/or the inlet opening of the assistive jet element can be from approximately 3 cm to approximately 4.5 cm from a proximal edge of the aspiration opening.

Additionally, in any of embodiments, the assistive jet from either the assistive jet channel or the assistive jet opening can be directed at a proximal side of the thrombus. The proximal side of the thrombus is the side of the thrombus that is closest to the proximal end of the aspiration catheter. A benefit of this arrangement is that, when the assistive jet from either the assistive jet channel or assistive jet opening is directed at a proximal side of the thrombus, the result will be that the proximal side of the thrombus will be sheared or broken up. This arrangement facilitates the easy aspiration of the sheared off or broken off pieces of the thrombus, because the sheared off or broken off thrombus will be directly exposed to the aspiration flow through the aspiration lumen. This can also reduce the likelihood that any sheared off or broken off pieces of thrombus will be released into the patient's vasculature.

The shape and size of the assistive jet inlet opening or aperture can be varied. In any embodiments, the inlet aperture or opening of the assistive jet element can have a round shape, a triangular shape, an oval shape, a longitudinal slit, or circumferential slit at the bottom of the aspiration around the aspiration lumen opening location. The aperture can be less than approximately 3 mm in any dimension to avoid weakening the catheter body. Weakening the catheter body can lead to kinking of the catheter body. A non-round geometry can increase the area of interaction and the volume/size of the assistive jet hitting the stuck thrombus. In some embodiments, an assistive jet opening size of 0.3 mm to 0.6 mm diameter hole can help promote the best mechanical integrity, and may not limit the flow through the bottom aperture. An approximately 0.3 mm size can be, in some embodiments, slightly superior since the velocity of the flow on the top is higher than that of the 0.6 mm. This also means greater aspiration power. The top and bottom jets can work together and provide better suction and a higher velocity into the lumen in the normal state, i.e. before clogging. For some embodiments, a 0.6 mm size can achieve a wider and stronger flow from the aperture than a 0.3 mm size when the aspiration lumen is in a blocked state. In some embodiments, this flow pattern can remain unchanged when opening sizes are above 0.6 mm.

In any embodiments, the catheter body can have an angled or beveled distal tip. The angle can be approximately 30 degrees, or from approximately 20 degrees to approximately 40 degrees or more, or from approximately 10 degrees or less (as little as 5 degrees) to approximately 50 degrees or more. In an angled configuration, an end of the catheter tip can be truncated, blunted, and/or rounded such that only a portion of the tip is angled or beveled. For example, the aspiration opening can have multiple angles and curves, ranging from 5 degrees to 45 degrees relative to the longitudinal axis of the catheter body. The opening for the assistive jet element can be positioned adjacent to any desired portion of the aspiration opening or window. Additionally, in any embodiments, an end of the aspiration catheter can have a straight cut.

For designs of the aspiration catheter that have a guidewire lumen (for example, the rapid exchange configurations disclosed herein), a 0.014 in guidewire compatible aspiration catheter can have a guidewire lumen of approximately 0.0165 in. Embodiments adapted for coronary applications can have a lumen sized for an approximately 0.014 in wire system. For lower limb applications, both 0.014 in and 0.018 in guidewire compatible systems can be used. If an 0.018 in system is used, the guidewire lumen can be approximately 0.0205 in in diameter.

Figure 4:
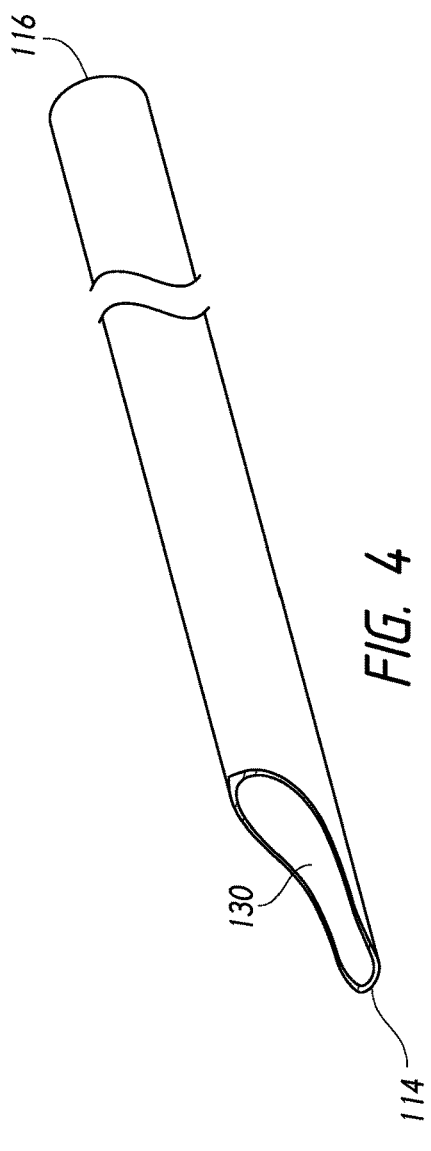
FIG. 4 is a perspective view of the assistive jet catheter body shown in FIG. 2.

FIG. 1 is a side view of an embodiment of an assistive jet aspiration catheter system 100 having a suction source 102 (which can be a Vaclok 30 cc syringe, a pump system such as a Penumbra™ pump, or otherwise), a stopcock or valve 104 to control the suction and flow of fluid through the system 100, and an assistive jet aspiration catheter 110 (also referred to herein as a assistive jet catheter and just an aspiration catheter). The assistive jet aspiration catheter 110 can have a catheter body 112 having a distal end 114 in a proximal end 116. A handle or hub 120 can be positioned at a proximal end of the catheter body. A strain relief component (such as strain relief component 117 shown in FIG. 1) can be positioned over the catheter body in any embodiments disclosed herein. The strain relief component can be positioned distal to the hub to reduce the strain experienced by the catheter body in that region. In any embodiments disclosed herein, the hub can be coupled directly or indirectly with a Y connector and/or the other components of the assistive jet aspiration catheter system 100. The Y connector can provide a sealed exit point from the aspiration lumen for a guidewire, for example, for the over-the-wire configuration embodiments. The catheter body can extend through the hub. The hub 120 can be used to rotate and otherwise manipulate the catheter body 112. FIG. 2 is a side view of the assistive jet catheter body 112 of the embodiment of the assistive jet aspiration catheter system 100 shown in FIG. 1. FIGS. 3 and 4 are a top view and a perspective view, respectively, of the assistive jet catheter body 112 shown in FIG. 2. FIG. 5 is a section view of the assistive jet catheter 110 shown in FIG. 2, taken through line 5-5 of FIG. 2, and FIG. 6 is a section view of the assistive jet catheter 110 shown in FIG. 2, taken through line 6-6 of FIG. 3.

With reference to the figures, in any embodiments, the catheter body 112 can have an aspiration opening 130 and an aspiration lumen 132 in communication with the aspiration opening 130 and extending through an entire length of the catheter body 112. In any embodiments disclosed herein, the aspiration opening can also be referred to as an aspiration window. The catheter body 112 can also have an assistive jet element 134 configured to direct a flow or jet of fluid (such as blood) into the aspiration lumen adjacent to the aspiration opening, as described herein. The assistive jet element 134 can comprise an assistive jet inlet opening 140 (also referred to herein as an assistive jet inlet) formed through the catheter body 112 at any desired radial and/or longitudinal location. In the illustrated embodiment, the assistive inlet flow opening can be positioned at a diametrically opposite position as compared to the most proximal portion of the aspiration opening 130. This can provide the most optimal flow of fluid toward a thrombus that may be lodged in the aspiration opening 130 to erode or break apart the thrombus. In any embodiments, the distal tip can be designed to be soft or flexible and atraumatic so as to reduce the risk of puncture and/or injury to the tissue as the catheter body is being advanced through the patient's vessel or passageway.

The aspiration opening 130 can have a curved profile with rounded edges. This curved profile can optimize the aspiration capabilities of the catheter body 112. In any other embodiments, the aspiration opening 130 can have a flat, angled or beveled profile, or even a square end profile. With reference to FIG. 6, the aspiration opening 130 can define any suitable angle A1. For example and without limitation, the angle A1 can be approximately 20°, or from approximately 10° to approximately 30°. Additionally, in any embodiments, a length of the aspiration opening L3 can be approximately 6 mm, or from approximately 5 mm or less to approximately 8 mm or more. The distal most tip 114 can be rounded or blunted again to reduce the risk of trauma to the tissue.

Figure 6:
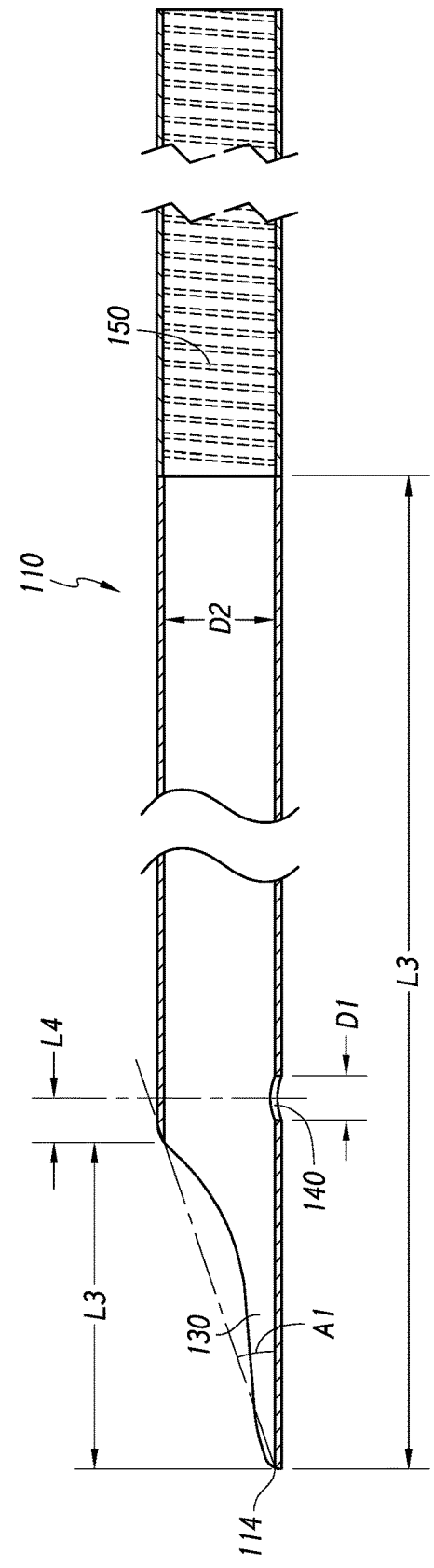
FIG. 6 is a section view of the assistive jet catheter body shown in FIG. 2, taken through line 6-6 of FIG. 3.

With reference to FIGS. 1 and 6, some embodiments of the aspiration catheter 110 can have a length L1 from approximately 90 cm to approximately 170 cm, which can be used for most neurological, coronary, vascular, and/or peripheral procedures for most radial and femoral access sites. However, the length of the catheter can be less than or greater than these values for any suitable applications. In any embodiments, a length L2 of the distal portion of the catheter body 112 can be approximately 7.4 mm or more, wherein the distal portion is defined as the region of the catheter body 112 that is unreinforced (i.e., where the catheter body does not have a braid or coil reinforcement). With a 7 mm long aspiration opening 130, and the assistive jet inlet 140 having a 0.3 mm diameter D1, the proximal braid section can be as close as 7.4 mm to the distal end 114. However, in any other embodiments, the braid or coil reinforcement can terminate at point proximal to 7.4 mm to fit the needs of the application. The proximal portion can have braids and/or coils 150 for reinforcement. The proximal portion can extend the rest of the length of the catheter body 112 from the proximal most end of the distal portion all the way to the proximal end 116 of the catheter body.

The location of the assistive jet inlet 140 relative to the aspiration opening 130 can have a significant impact on the effectiveness of the assistive jet element to provide the flow or jet of fluid needed to break down or erode thrombus stuck in the aspiration opening 130. For example, if the assistive jet inlet 140 is too far distal, there will be a risk that the assistive jet opening 140 will also be clogged by a thrombus that has clogged the aspiration opening 130. If the assistive jet inlet 140 is too far proximal, the ability of the assistive jet inlet 140 to direct a sufficient jet or flow of fluid at a thrombus lodged in the aspiration opening 130 can be attenuated thereby reducing the effectiveness of the assistive jet element 134. In some embodiments, the assistive jet inlet 140 can be positioned such that an axial centerline of the assistive jet inlet 140 is at a distance L4 of approximately 1 mm, or from approximately −2 mm to approximately 10 mm (the negative number indicates that the axial centerline of the opening is positioned distal to the proximal edge of the aspiration opening), or from approximately 1 mm to approximately 3 mm, from the proximal most end of the aspiration opening 130, or to and/or from any values within these ranges. In some embodiments, the assistive jet inlet 140 can be positioned such that the centerline of the assistive jet inlet 140 is positioned distal of the proximal most end, which can increase the impact of flow through the inlet 140 against the thrombus, assuming that the inlet 140 is not clogged by or covered by the thrombus.

In any embodiments disclosed herein, the assistive jet inlet 140 can have diameter D1 that is approximately ⅓ (33%) of a diameter D2 of the aspiration lumen 132, or from approximately 10% to approximately 15% for 3 Fr (i.e., French size) compatible catheter, or from approximately 25% to approximately 45% of the diameter of the aspiration lumen 132. If the diameter of the assistive jet inlet 140 is too large relative to the aspiration lumen, the assistive jet inlet 140 can draw more flow from the surrounding fluid that is optimal or desired even when the aspiration opening 130 is not clogged. The same condition can occur if the assistive jet inlet 140 is positioned too close to the aspiration opening 130. In any embodiments disclosed herein, the aspiration flow inlet 140 can have a round, oblong, ovular, triangular, or any other suitable shape.

In any embodiments, the assistive jet element can have a plurality of holes or inlets through the catheter body to provide additional flow or jet pathways toward a thrombus stuck in the aspiration window. The number of holes, position of the holes, and diameter of the holes can depend largely on the type of thrombus to be removed. The number of holes should be optimized to provide effective erosion of the thrombus while not significantly reducing the amount of suction or flow through the aspiration opening 130. Too many aspiration flow inlets in the catheter body, or the diameter of the aspiration flow inlets is too large, can result in too significant of a pressure drop that can reduce the effectiveness of the assistive jet elements, basically the flow through each of the assistive jet inlets can be too weak to significantly erode the thrombus. Without limitation, the assistive jet inlets can be positioned at approximately 3 o'clock and 9 o'clock, or approximately 3 o'clock, 6 o'clock, and 9 o'clock.

In any embodiments, the diameter D2 of the aspiration lumen 130 (see FIG. 6) can be any suitable value for the application and size constraint of a particular application. For example and without limitation, in some embodiments, for a 4.2 Fr guide sheath, the maximum outer diameter of an aspiration catheter body that would function optimally (i.e., draw flow from the surrounding fluid, etc.) with such a guide sheath is approximately 1.22 mm. A suitable assistive jet inlet diameter for this configuration is approximately 0.26 mm, which can have an aspiration lumen having a cross-sectional area of approximately 0.49 mm$^2$. In some embodiments, for a 6 Fr guide sheath, the maximum outer diameter of an aspiration catheter body that would function optimally (i.e., draw flow from the surrounding fluid, etc.) with such a guide sheath is approximately 2.16 mm, which can have an aspiration lumen having a cross-sectional area of approximately 2.7 mm$^2$. A suitable assistive jet inlet diameter for this configuration is approximately 0.62 mm. In some embodiments, for an 8 Fr guide sheath, the maximum outer diameter of an aspiration catheter body that would function optimally (i.e., draw flow from the surrounding fluid, etc.) with such a guide sheath is approximately 2.82 mm, which can have an aspiration lumen having a cross-sectional area of approximately 4.97 mm$^2$. A suitable assistive jet inlet diameter for this configuration is approximately 0.84 mm.

Additionally, even though a diameter value is stated for the assistive jet inlet, the assistive jet inlet in this and all other embodiments disclosed herein can have a non-circular shape. For the embodiments having a non-circular shape, the size of the non-circular assistive jet inlets can be of an equivalent cross-sectional area and/or size. Further, any of the values listed in this description for the diameter of the assistive jet inlet can be substituted for ranges extending from 20% less than the stated value to 20% greater than the stated value, or from 10% less than the stated value to 10% greater than the stated value. For example and without limitation, for the 6 Fr compatible aspiration catheter, the diameter of the assistive jet inlet can be from approximately 0.496 mm to approximately 0.744 mm, or from 0.558 mm to approximately 0.682 mm, while the other values of each embodiment can be adjusted accordingly to ensure optimal fit and performance of such embodiment.

Further, any embodiments can have one or more radiopaque bands or markers near the aspiration opening 130 or assistive jet inlet 140, so that a physician can identify the location of these features under fluoroscopy. Alternatively or in combination with such bands or markers, certain portions of the catheter 110 can comprise a radiopaque material to improve the visibility of such portions under fluoroscopy.

Figure 7:
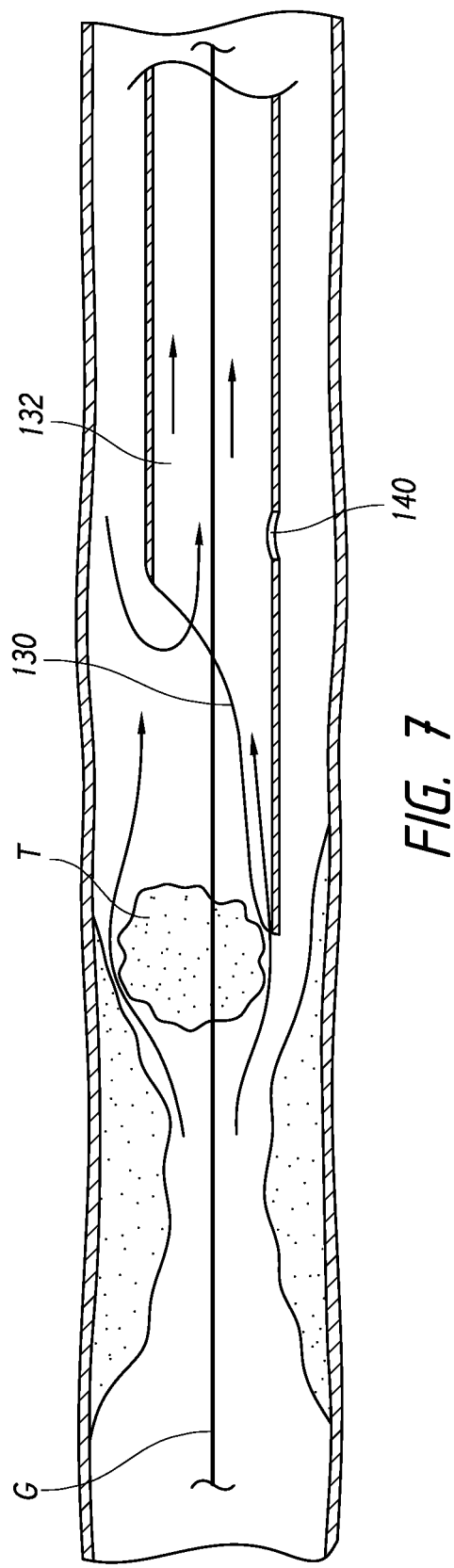
FIG. 7 is a section view of the assistive jet catheter body shown in FIG. 2, illustrating aspiration of a mass of thrombus.

FIG. 7 is a section view of the assistive jet catheter body 112, illustrating aspiration of a mass of thrombus T that is located distal to or upstream of the aspiration opening 130 of the assistive jet catheter body 112. Because the flow of fluid through the aspiration opening 130 is not impeded by thrombus or otherwise, the flow of blood (indicated by the flow arrows) through the assistive jet inlet 140 is significantly diminished such that all or most of the flow through the aspiration lumen 132 will go through the aspiration opening 130. The guidewire G can be maintained in the aspiration lumen 132 during the aspiration procedures, or can be withdrawn partially or completely from the aspiration lumen prior to performing the aspiration procedures.

Figure 8:
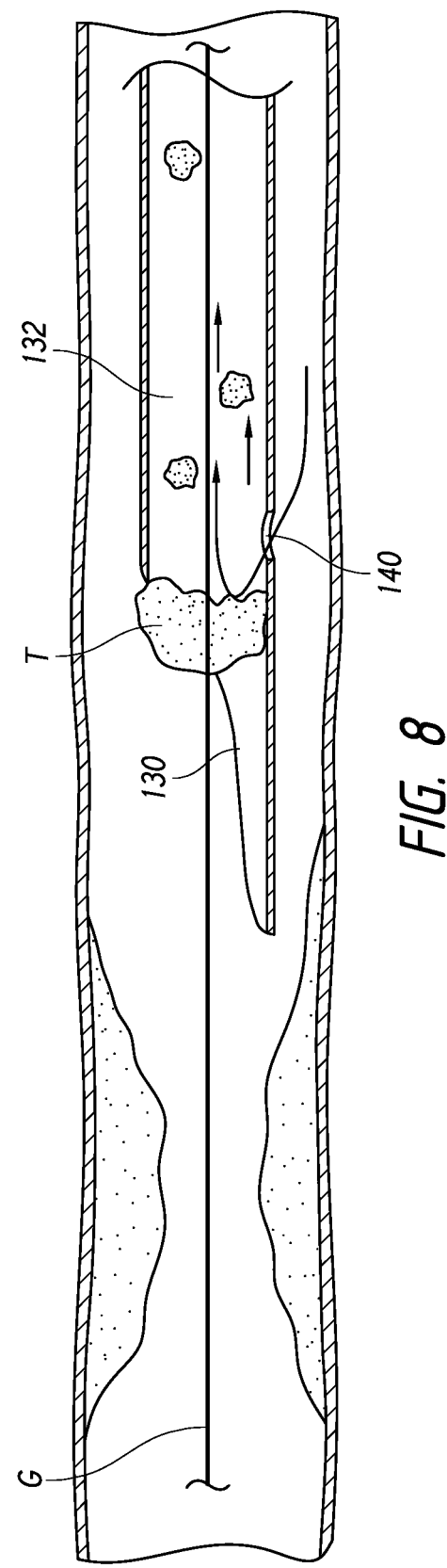
FIG. 8 is a section view of the assistive jet catheter body shown in FIG. 2, illustrating aspiration of a mass of thrombus.

FIG. 8 is a section view of the assistive jet catheter shown in FIG. 2, illustrating aspiration of a mass of thrombus T that is located in contact with the aspiration opening 130 of the assistive jet catheter body 112 such that the thrombus T is blocking all or most of the flow through the aspiration opening 130. In this state, because the flow of fluid through the aspiration opening 130 is substantially diminished or is zero, fluid or blood can be drawn through the assistive jet inlet 140 and into the aspiration lumen 132. The assistive jet inlet 140 can be sized and positioned to optimally direct or exert the flow through the assistive jet inlet toward or against the thrombus, so as to break apart or erode the thrombus T. The jet or flow of blood through the assistive jet inlet 140 can eventually break down the thrombus T to a small enough size such that the thrombus T can be aspirated through the aspiration lumen 132, thereby once again reactivating flow through the aspiration opening 130.

Figure 9:
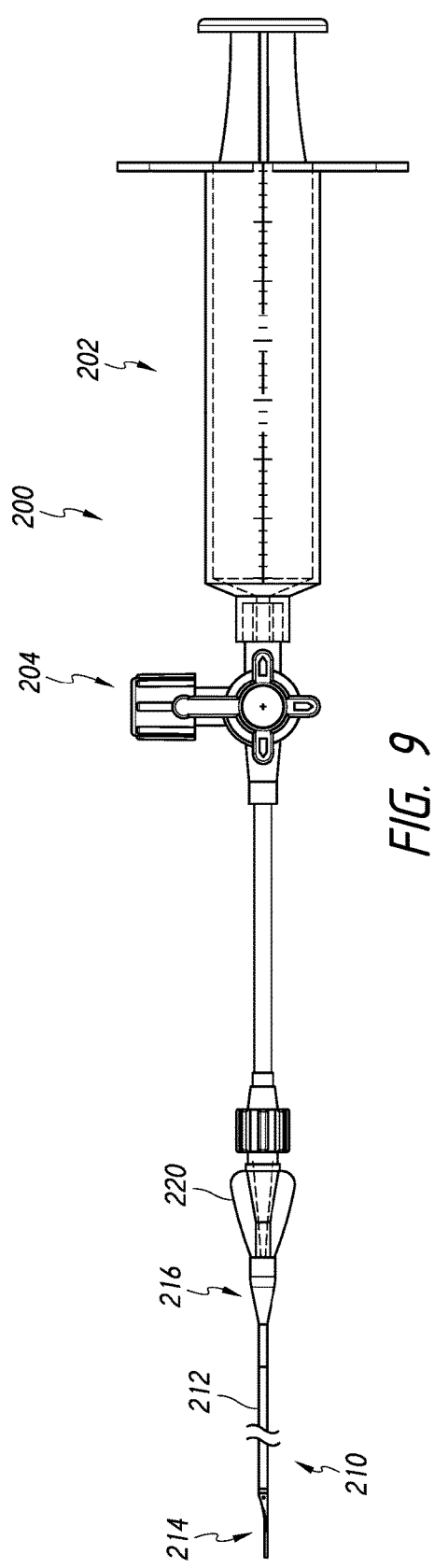
FIG. 9 is a side view of another embodiment of an aspiration catheter system, this embodiment being of a rapid exchange configuration, showing a portion of the catheter in a loop to reduce the size of the figure.

FIG. 9 is a side view of another embodiment of an assistive jet aspiration catheter system 200, this embodiment being of a rapid exchange configuration. Any embodiments of the catheter 200 can have any of the other features, components, materials, dimensions, and/or other details of any of the other catheter system embodiments disclosed herein, in combination with or in place of any of the features, components, materials, dimensions, and/or other details disclosed with respect to the embodiments of the catheter system 200 described below to form new embodiments. Similarly, any of the other catheter system embodiments disclosed herein can have any of the features, components, materials, dimensions, and/or other details described herein with respect to the catheter system 200 in combination with or in place of any of the features, components, materials, dimensions, and/or other details disclosed with respect to the embodiment of the other catheter systems. For efficiency, a description of the components and features that are common between the catheter system 200 and catheter system 100 will be omitted.

Figure 10:
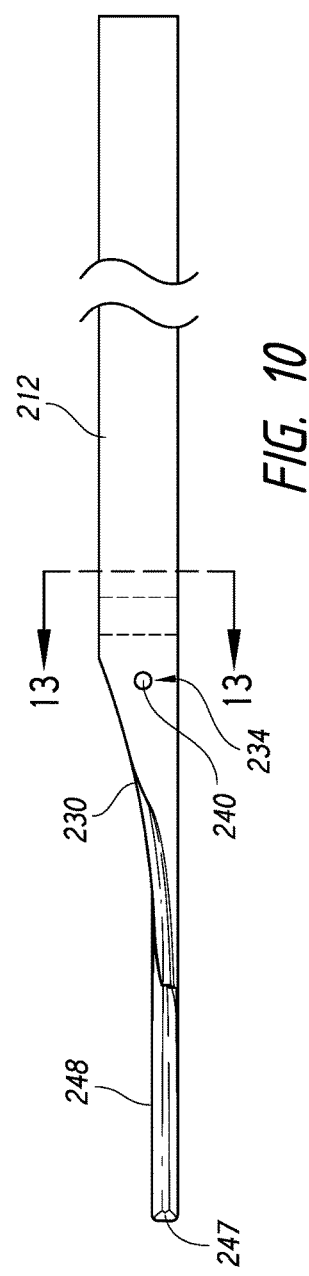
FIG. 10 is a side view of the assistive jet catheter body of the embodiment of the assistive jet aspiration catheter system shown in FIG. 9.
Figure 11:
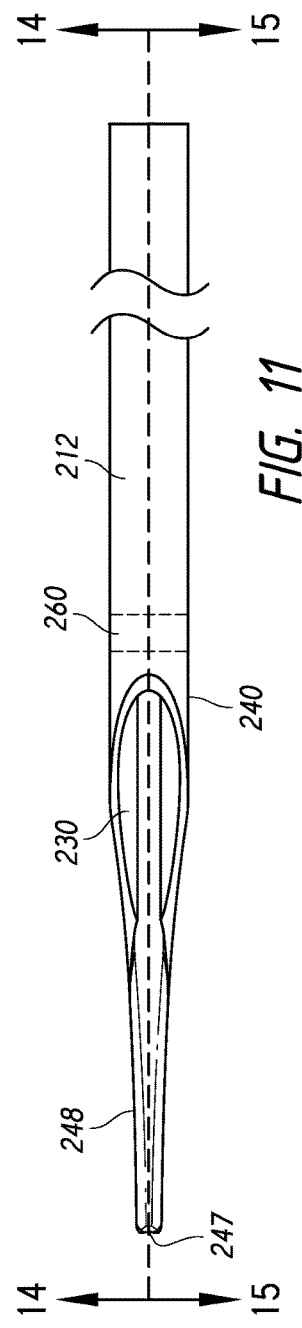
FIG. 11 is a top view of the assistive jet catheter body shown in FIG. 10.
Figure 13:
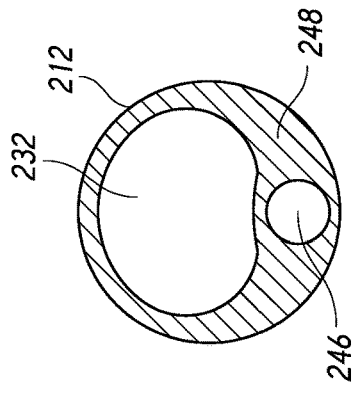
FIG. 13 is a section view of the assistive jet catheter body shown in FIG. 10, taken through line 13-13 of FIG. 10.
Figure 12:
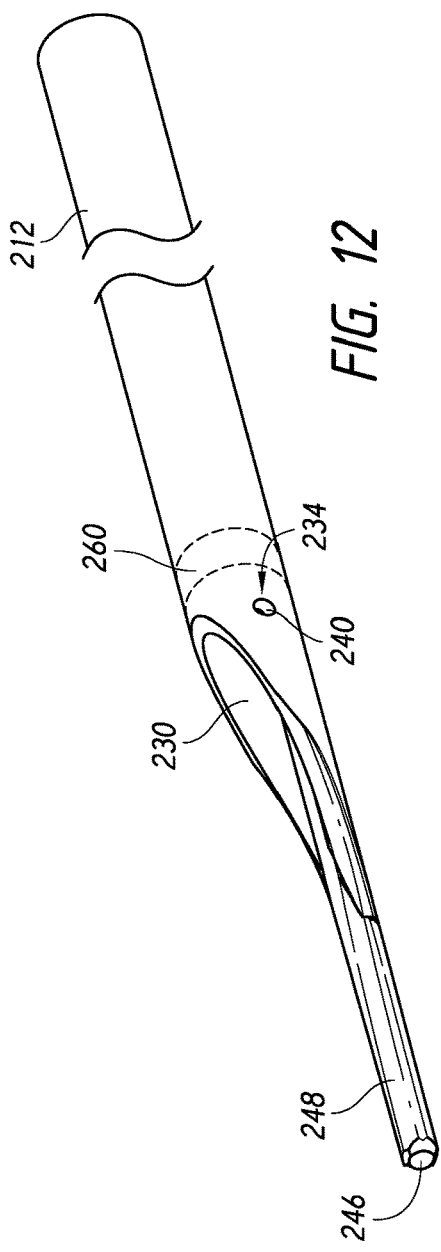
FIG. 12 is a perspective view of the assistive jet catheter body shown in FIG. 10.
Figure 14:
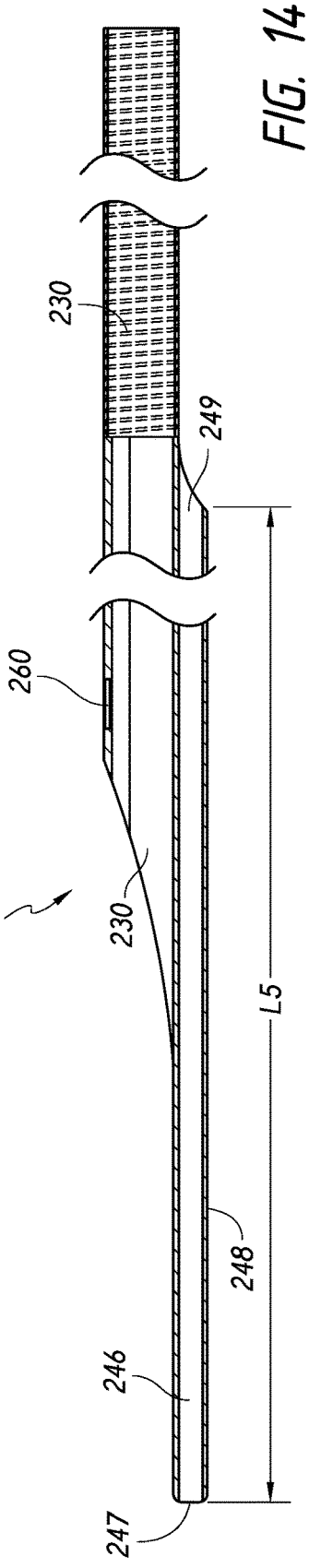
FIG. 14 is a section view of the assistive jet catheter body shown in FIG. 10, taken through line 14-14 of FIG. 11.
Figure 15:
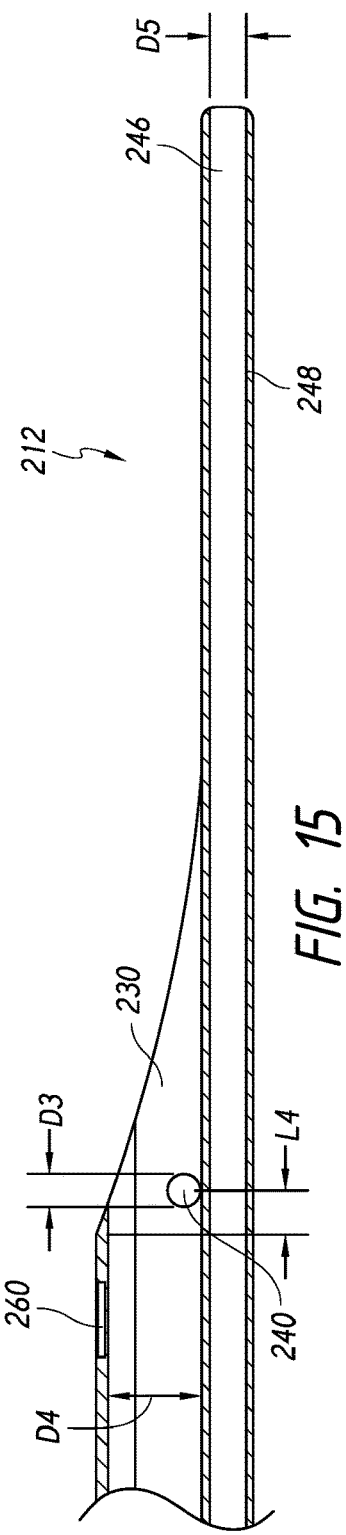
FIG. 15 is a section view of a portion of the assistive jet catheter body shown in FIG. 10, taken through line 15-15 of FIG. 11.

FIGS. 10, 11, and 12 are a side view, a top view, and a perspective view, respectively, of the assistive jet catheter body 212 of the embodiment of the assistive jet aspiration catheter system 200 shown in FIG. 9. FIG. 13 is a section view of the assistive jet catheter body 212, taken through line 13-13 of FIG. 10. FIG. 14 is a section view of the assistive jet catheter body 212, taken through line 14-14 of FIG. 11, and FIG. 15 is a section view of the assistive jet catheter body shown in FIG. 10, taken through line 15-15 of FIG. 11.

The assistive jet aspiration catheter system 200 can have a suction source 202 (which can be a Vaclok 30 cc syringe, a pump system such as a Penumbra™ pump, or otherwise), a stopcock or valve 204 to control the suction and flow of fluid through the system 200, and an assistive jet aspiration catheter 210 (also referred to herein as an assistive jet catheter and just an aspiration catheter) having a catheter body 212 having a distal end 214 in a proximal end 216. A handle 220 can be positioned at a proximal end of the catheter body. A guidewire lumen 246 can extend through a guidewire channel 248 that can extend through at least a portion of the aspiration catheter body 212. The guidewire lumen 246 can have a first opening 247 at a distal end 214 of the catheter body 212 and a second opening 249 proximal to the first opening. The guidewire channel 248 can be used for rapid exchange guidewire procedures.

With reference to the figures, in any embodiments, the catheter body 212 can have an aspiration opening 230 and an aspiration lumen 232 in communication with the aspiration opening 230 and extending through an entire length of the catheter body 212. The catheter body 212 can also have an assistive jet element 234 configured to direct a flow or jet of fluid (such as blood) into the aspiration lumen adjacent to the aspiration opening, as described herein. The assistive jet element 234 can comprise an assistive jet inlet opening 240 (also referred to herein just as an assistive jet inlet) formed through the catheter body 212 at any desired radial and/or longitudinal location. In the illustrated embodiment, the assistive inlet flow opening can be positioned at lateral or side wall position when the catheter body is in an upright position wherein a guidewire lumen 246 is in the downward or vertically lowermost position. This can provide the most optimal flow of fluid toward a thrombus that may be lodged in the aspiration window or opening 230 to erode or break apart the thrombus. Alternatively, the assistive jet opening 240 can be positioned at any desired radial position on the catheter body 212.

Similar to catheter body 112 described above, the catheter body 212 can have a proximal section and a distal section. The proximal section of the catheter body 212 can be reinforced similar to the proximal section of the catheter body 112 described above, the details of which are omitted herein for efficiency.

In any embodiments, the distal tip comprising a guidewire channel 248 can be designed to be soft or flexible and atraumatic so as to reduce the risk of puncture and/or injury to the tissue as the catheter body is being advanced through the patient's vessel or passageway. The guidewire lumen 246 can extend through the guidewire channel 248 that can extend distally away from the catheter body 212. The assistive jet inlet is optimally positioned to pass through a side of the catheter body 212 to avoid the guidewire channel 248.

Similar to the aspiration opening 130, the aspiration opening 230 can have a curved profile with rounded edges. This curved profile can optimize the aspiration capabilities of the catheter body 212. In any other embodiments, the aspiration opening 230 can have a flat, angled or beveled profile, or even a square end profile (except for the guidewire channel 248). The length of the catheter body 212 can be approximately the same as or similar to the length of the catheter body 112, including or excluding the portion of the guidewire channel 248 that extends distally away from the catheter body 212 distal to the aspiration opening 230.

The location of the assistive jet inlet 240 relative to the aspiration opening 230 can have a significant impact on the effectiveness of the assistive jet element to provide the flow or jet of fluid needed to break down or erode thrombus stuck in the aspiration opening 230. In some embodiments, the assistive jet inlet 240 can be positioned such that a centerline of the assistive jet inlet 240 is at a distance L4 of approximately 1 mm, or from approximately 0 mm to approximately 5 mm, or from approximately 1 mm to approximately 3 mm, from the proximal most end of the aspiration opening 230. In some embodiments, the assistive jet inlet 240 can be positioned such that the centerline of the assistive jet inlet 240 is positioned distal of the proximal most end, which can increase the impact of flow through the inlet 240 against the thrombus, assuming that the inlet 240 is not clogged by or covered by the thrombus.

In any embodiments disclosed herein, the assistive jet inlet 240 can have a diameter that is approximately ⅓ (33%) of the diameter of the aspiration lumen 232, or from approximately 10% to approximately 15% for 3 Fr compatible catheter, or from approximately 25% to approximately 45% of the diameter of the aspiration lumen 232. In any embodiments disclosed herein, the aspiration flow inlet 240 can have a round, oblong, ovular, triangular, or any other suitable shape.

In any embodiments, the assistive jet element can have a plurality of holes or inlets through the catheter body to provide additional flow or jet pathways toward a thrombus stuck in the aspiration window. Without limitation, the assistive jet inlets can be positioned at approximately 3 o'clock and 9 o'clock, or approximately 3 o'clock, 6 o'clock, and 9 o'clock.

In any embodiments, a diameter of the aspiration lumen D4 (see FIG. 15) can be any suitable value for the application and size constraint of a particular application. For example and without limitation, in some embodiments, for a 4.2 Fr guide sheath, the maximum outer diameter of an aspiration catheter body that would function optimally (i.e., draw flow from the surrounding fluid, etc.) with such a guide sheath can be approximately 1.22 mm. A suitable assistive jet inlet diameter for this configuration can be approximately 0.11 mm, which can have an aspiration lumen having a cross-sectional area of approximately 0.086 mm$^2$. In some embodiments, for a 6 Fr guide sheath, the maximum outer diameter of an aspiration catheter body that would function optimally (i.e., draw flow from the surrounding fluid, etc.) with such a guide sheath can be approximately 2.16 mm, which can have an aspiration lumen having a cross-sectional area of approximately 1.65 mm$^2$. A suitable assistive jet inlet diameter for this configuration can be approximately 0.483 mm. In some embodiments, for an 8 Fr guide sheath, the maximum outer diameter of an aspiration catheter body that would function optimally (i.e., draw flow from the surrounding fluid, etc.) with such a guide sheath can be approximately 2.82 mm, which can have an aspiration lumen having a cross-sectional area of approximately 3.16 mm$^2$. A suitable assistive jet inlet diameter for this configuration can be approximately 0.669 mm. The foregoing values are merely examples and can vary.

Additionally, even though a diameter value is stated for the assistive jet inlet, the assistive jet inlet in this and all other embodiments disclosed herein can have a non-circular shape. For the embodiments having a non-circular shape, the size of the non-circular assistive jet inlets can be of an equivalent cross-sectional area and/or size. Further, any of the values listed in this description for the diameter of the assistive jet inlet can be substituted for ranges extending from 20% less than the stated value to 20% greater than the stated value, or from 10% less than the stated value to 10% greater than the stated value. For example and without limitation, for the 6 Fr compatible aspiration catheter, the diameter of the assistive jet inlet can be from approximately 0.386 mm to approximately 0.580 mm, or from 0.435 mm to approximately 0.531 mm, while the other values of each embodiment can be adjusted accordingly to ensure optimal fit and performance of such embodiment.

Further, any embodiments can have one or more radiopaque bands or markers 260 near the aspiration opening 230 or assistive jet inlet 240, so that a physician can identify the location of these features under fluoroscopy. Alternatively or in combination with such bands or markers, certain portions of the catheter 210 can comprise a radiopaque material to improve the visibility of such portions under fluoroscopy.

In any embodiments, a length L5 (shown in FIG. 14) of the guidewire channel 248 can be approximately 15 cm, or can be from approximately 10 cm to approximately 15 cm, or from approximately 5 cm to approximately 15 cm. A diameter D5 of the guidewire lumen can be approximately 0.016 in for a system using 0.014 in guidewire. The diameter D5 of the guidewire lumen in larger systems, such as systems having catheters greater than 14 Fr that are configured to use a 0.018 in guidewire can be approximately 0.020 in. The diameter D5 of the guidewire lumen in systems having catheters greater than 18 Fr that are configured to use a 0.035 in guidewire can be approximately 0.037 in.

FIG. 16 is a section view of the assistive jet catheter body 212, illustrating aspiration of a mass of thrombus T that is located distal to or upstream of the aspiration opening 230 of the assistive jet catheter 210. Because the flow of fluid through the aspiration opening 230 is not impeded by thrombus or otherwise, the flow of blood (indicated by the flow arrows in FIG. 16) through the assistive jet inlet 240 is significantly diminished such that all or most of the flow through the aspiration lumen 232 will go through the aspiration opening 230.

FIG. 17 is a section view of the assistive jet catheter body 212, illustrating aspiration of a mass of thrombus T that is located in contact with the aspiration opening 230 of the assistive jet catheter body 212 such that the thrombus T is blocking all or most of the flow through the aspiration opening 230. In this state, because the flow of fluid through the aspiration opening 230 is substantially diminished or is zero, fluid or blood can be drawn through the assistive jet inlet 240 and into the aspiration lumen 232. The assistive jet inlet 240 can be sized and positioned to optimally direct or exert the flow through the assistive jet inlet toward or against the thrombus, so as to break apart or erode the thrombus T. The jet or flow of blood through the assistive jet inlet 240 can eventually break down the thrombus T to a small enough size such that the thrombus T can be aspirated through the aspiration lumen 232, thereby once again reactivating flow through the aspiration opening 230. The guidewire G can be maintained in the aspiration lumen 232 during the aspiration procedures, or can be withdrawn partially or completely from the aspiration lumen prior to performing the aspiration procedures.

In some embodiments, the assistive jet element can comprise one or more assistive jet channels that can direct a jet of fluid against a thrombus adjacent to or plugging an aspiration opening. The assistive jet channel can extend between a first opening and a second opening. The first opening can be positioned closer to a proximal end of the catheter body as compared to the second opening. The first opening can be positioned to be in direct contact or be directly exposed to the fluid flow within the vessel. The first opening can extend through an outer wall of the catheter body. In this configuration, blood can flow directly into the first opening, through the assistive jet channel, and out through the second opening. In some embodiments, the first opening can be referred to as an inlet opening or aperture, and the second opening can be referred to as an outlet opening or aperture.

The cross-sectional shape of the channel in any embodiments can be round, square, ovular, oblong, or otherwise. Ideally, the shape is oblong along the length, lengthening the hole by 0.5 to 3 mm, such that blood can flow into the channel with less velocity and energy loss. In any embodiments disclosed herein, the assistive jet channel can have an approximately oblong shape.

In any embodiments, the assistive jet catheter system can have an embedded or integral assistive jet channel or lumen on an inside surface of the aspiration lumen. In any embodiments, the assistive jet channel can be radially positioned such that the channel is adjacent to the most proximal portion or edge of the aspiration opening. In other words, in any embodiments disclosed herein, the assistive jet channel can be positioned adjacent or approximately adjacent to a portion of the aspiration opening that is closest to the proximal end of the catheter system, when the aspiration opening is tapered or slanted. In this arrangement, if a large mass of thrombus is drawn into the distal end of the catheter that has a size that is larger than a cross-sectional size of the aspiration lumen, such that the mass of thrombus cannot freely pass through the aspiration opening or aspiration lumen (thereby, presenting a clog or impediment to the distal end of the aspiration catheter), blood can still be drawn into the aspiration lumen through the assistive jet channel, which can create a jet of fluid that can break down the thrombus. Alternatively, in any embodiments disclosed herein, the assistive jet channel can be positioned such that a distal opening of the channel is positioned adjacent or approximately adjacent to a portion of the aspiration opening that is closest to the distal end of the catheter system, or anywhere between the proximal and distal edges of the aspiration opening.

Blood flowing out of the second opening (or outlet) of the assistive jet channel and into the aspiration lumen can exert a force on the clot adjacent to or abutting the aspiration opening that can cause the thrombus to break apart into smaller pieces that can pass through the aspiration opening and/or aspiration lumen. In essence, the assistive jet channel can produce a flow stream of blood from the patient's vasculature directed at the aspiration opening and/or thrombus or other debris that is positioned in contact with, adjacent to, or near the aspiration opening that can continuously break up the thrombus even when the thrombus covers up the aspiration opening and/or the opening at the end of the assistive jet channel.

In any embodiments, the assistive jet channel can have a cross-sectional size or area that is approximately 10% of the cross-sectional size or area of the aspiration lumen, or from approximately 5% to approximately 25% or more, or from approximately 10% to approximately 15% of the cross-sectional size or area of the aspiration lumen. Alternatively, the assistive jet channel can have a cross-sectional size that is larger than the sizes listed above, though the effectiveness of the shearing force directed to the thrombus by the assistive jet channel may be significantly reduced by the larger cross-sectional size of the assistive jet channel. In some embodiments, the cross-sectional size or area of the assistive jet channel can be greater than approximately 0.2 mm$^2$.

Additionally, in any embodiments having a relatively smaller catheter size (for example, from 3 Fr to 5 Fr), the assistive jet inlet opening (for an assistive jet opening, assistive channel, telescopic, or any other suitable configuration) can have a cross-sectional size or area that is from approximately 20% to approximately 50%, or from approximately 25% to approximately 35%, of the cross-sectional size or area of the aspiration lumen. In any embodiments having a larger catheter size (for example, 6 Fr and larger), the assistive jet inlet opening (for an assistive jet opening, assistive channel, telescopic, or any other suitable configuration) can have a cross-sectional size or area that is from approximately 10% to approximately 40%, or from approximately 20% to approximately 40%, of the cross-sectional size or area of the aspiration lumen.

For example and without limitation, in the 4.2 Fr compatible aspiration catheter (i.e., which can be used with a 4.2 Fr guide sheath), the catheter can have an outer diameter of approximately 1.22 mm or less, the cross-sectional area of the assistive jet channel can be approximately 0.003 mm$^2$, and a cross-sectional area of the aspiration lumen can be approximately 0.03 mm$^2$, though the cross-sectional area larger may be larger than this for optimal performance of the catheter. For a 6F compatible aspiration catheter, which can be used for coronary applications, the catheter can have an outer diameter of approximately 2.16 mm, the cross-sectional area of the assistive jet channel can be approximately 0.09 mm$^2$, and a cross-sectional area of the aspiration lumen can be approximately 0.83 mm$^2$. For an 8F compatible aspiration catheter, the catheter can have an outer diameter of approximately 2.82 mm, the cross-sectional area of the assistive jet channel can be approximately 0.18 mm$^2$, and a cross-sectional area of the aspiration lumen can be approximately 1.65 mm$^2$.

Any of the values listed in this description for the cross-sectional area of the assistive jet channel can be substituted for ranges extending from 20% less than the stated value to 20% greater than the stated value, or from 10% less than the stated value to 10% greater than the stated value. For example and without limitation, for the 6 Fr compatible aspiration catheter, the cross-sectional area of the assistive jet channel can be from approximately 0.0024 mm$^2$ to approximately 0.0036 mm$^2$, or from 0.0027 mm$^2$ to approximately 0.0033 mm$^2$, while the other values of each embodiment can be adjusted accordingly to ensure optimal fit and performance of such embodiment. Further, for any embodiments disclosed herein, the assistive jet channel in this and all other embodiments disclosed herein can have a non-circular shape.

The flow channel in any embodiments set forth herein can be in any of a variety of suitable or desired shapes (for example, circular or non-circular, including oblong, curved oblong, ovular, rectangular, or otherwise), sizes, and geometries. As mentioned above, the size of the channel can be varied, but should be large enough to permit adequate blood flow. The inlet opening should be positioned far enough away from the aspiration opening so as to be out of the targeted lesion to reduce the likelihood that the inlet opening will be clogged by thrombus. However, it may not be desirable for the inlet to be located too far away from the aspiration opening, as this can reduce the inlet flow velocity and volume in some embodiments.

In smaller applications, the size of the assistive jet element should be adequate to ensure that blood will flow substantially unimpeded through the assistive jet element, or flow through the assistive jet element without shearing the red blood cells. If the assistive jet element is too small, the flow of blood through the assistive jet element can be impeded.

In applications other than the coronary arteries, using a 7F system, the diameter of the assistive jet element in any embodiments disclosed herein can be (without limitation) from approximately 0.012 in to approximately 0.025 in, or from approximately 0.010 in to approximately 0.031 in. Using, an 8F system, the diameter of the assistive jet element in any embodiments disclosed herein can be (without limitation) from approximately 0.010 to approximately 0.028 in or more, or from approximately 0.014 to approximately 0.028 in. Using, an 9F system, the diameter of the assistive jet element in any embodiments disclosed herein can be (without limitation) from approximately 0.010 to approximately 0.032 in or more, or from approximately 0.014 to approximately 0.032 in. In a 5F system, the diameter of the assistive jet element in any embodiments disclosed herein can be (without limitation) from approximately 0.011 in to approximately 0.015 in, or from approximately 30% to 40% of the available lumen diameter or size.

FIG. 18 is a side view of an embodiment of an assistive channel aspiration catheter system 300, also being of a rapid exchange configuration. Any embodiments of the catheter 300 can have any of the other features, components, materials, dimensions, and/or other details of any of the other catheter system embodiments disclosed herein, in combination with or in place of any of the features, components, materials, dimensions, and/or other details disclosed with respect to the embodiments of the catheter system 300 described below to form new embodiments. Similarly, any of the other catheter system embodiments disclosed herein can have any of the features, components, materials, dimensions, and/or other details described herein with respect to the catheter system 300 in combination with or in place of any of the features, components, materials, dimensions, and/or other details disclosed with respect to the embodiment of the other catheter systems. For efficiency, a description of the components and features that are common between the catheter system 300 and catheter system 100 or catheter system 200 will be omitted.

Figure 21:
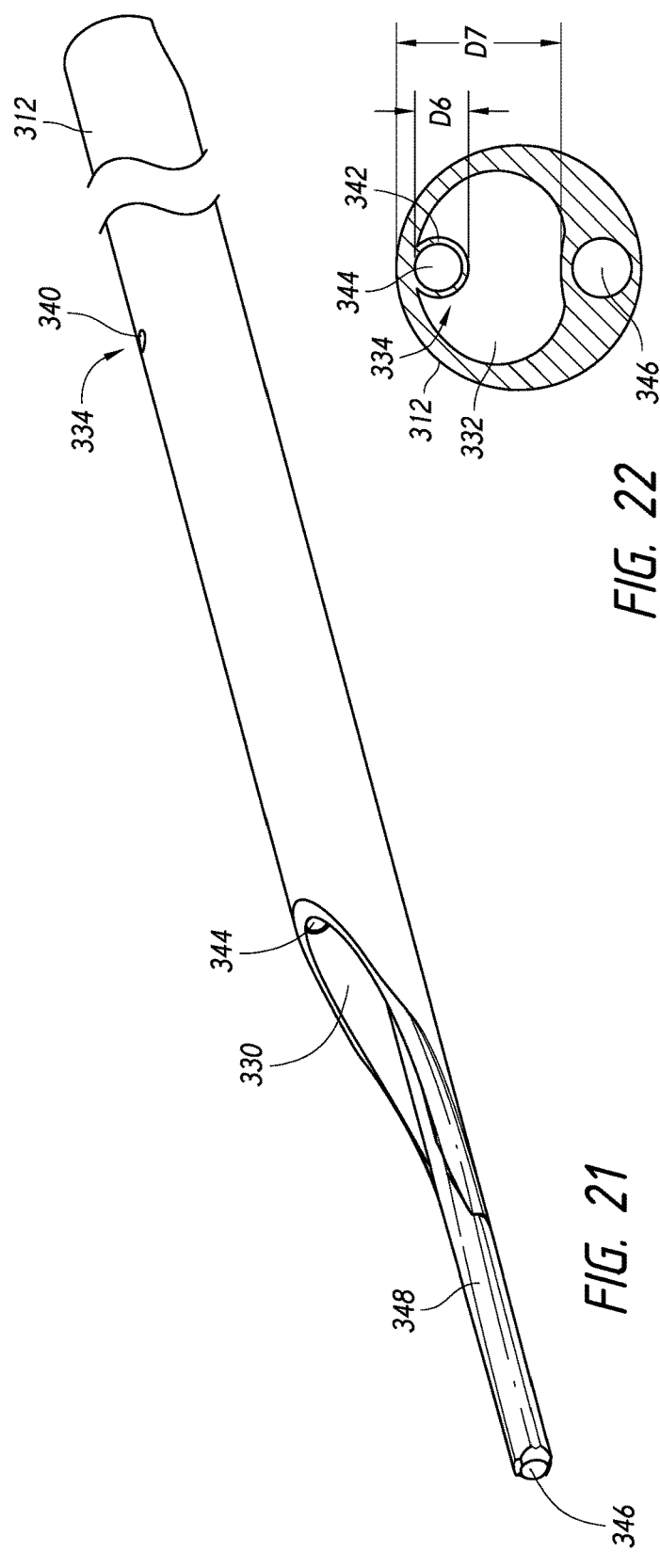
FIG. 21 is a perspective view of the assistive jet catheter body shown in FIG. 19.
Figure 22:
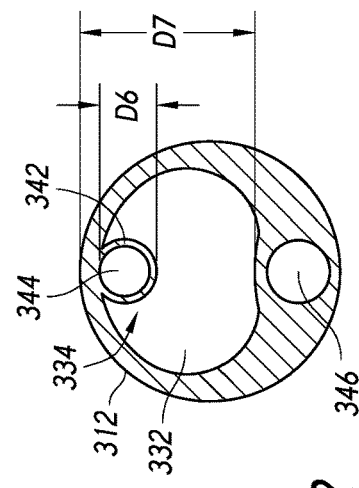
FIG. 22 is a section view of the assistive jet catheter body shown in FIG. 19, taken through line 22-22 of FIG. 19.
Figure 23:
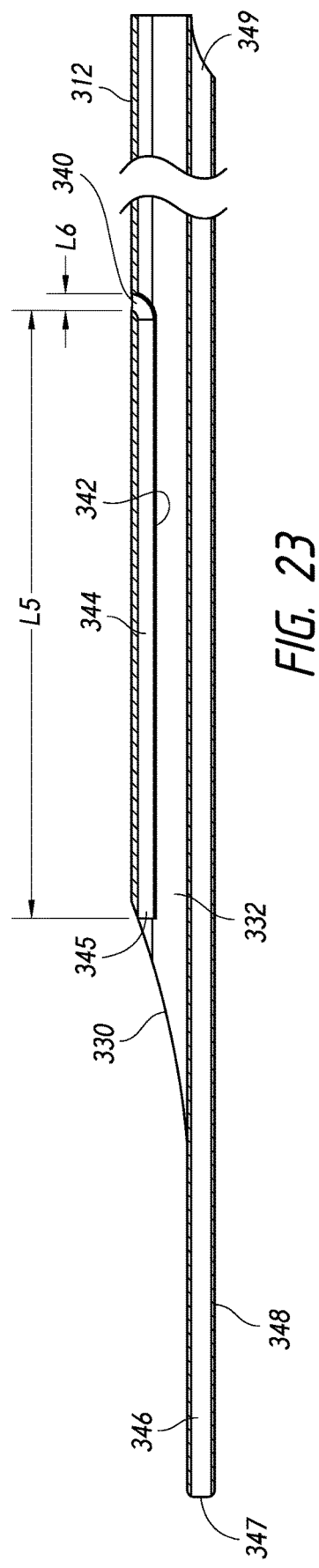
FIG. 23 is a section view of the assistive jet catheter body shown in FIG. 19, taken through line 23-23 of FIG. 20.

FIGS. 19, 20, and 21 are a side view, a top view, and a perspective view, respectively, of an assistive channel catheter body 312 of the embodiment of the assistive channel aspiration catheter system 300 shown in FIG. 18. FIG. 22 is a section view of the assistive channel catheter body 312, taken through line 22-22 of FIG. 19. FIG. 23 is a section view of the assistive channel catheter body 312, taken through line 23-23 of FIG. 20.

The assistive channel aspiration catheter system 300 can have a suction source 302 (which can be a Vaclok 30 cc syringe, a pump system such as a Penumbra™ pump, or otherwise), a stopcock or valve 304 to control the suction and flow of fluid through the system 300, and an assistive channel aspiration catheter 310 (also referred to herein as an assistive channel catheter and just an aspiration catheter) having a catheter body 312 having a distal end 314 in a proximal end 316. A handle or hub 320 can be positioned at a proximal end of the catheter body. A guidewire lumen 346 can have a first opening 347 at a distal end 314 of the catheter body 312 and a second opening 349 proximal to the first opening. The guidewire channel 348 can be used for rapid exchange guidewire procedures.

With reference to the figures, in any embodiments, the catheter body 312 can have an aspiration window or opening 330 and an aspiration lumen 332 in communication with the aspiration opening 330 and extending through an entire length of the catheter body 312. The catheter body 312 can also have an assistive jet element 334 configured to direct a flow or jet of fluid (such as blood) into the aspiration lumen adjacent to the aspiration opening, as described herein. The assistive jet element 334 can comprise an assistive channel inlet or channel opening 340 (also referred to herein just as an assistive channel inlet) formed through the catheter body 312 at any desired radial and/or longitudinal location. In the illustrated embodiment, the assistive inlet flow opening can be positioned at a top wall position when the catheter body is in an upright position wherein a guidewire lumen 346 is in the downward or vertically lowermost position so that the assistive flow element 334 is closest to a proximal edge of the aspiration opening 330. This can provide the most optimal flow of fluid toward a thrombus that may be lodged in the aspiration opening 330 to erode or break apart the thrombus. Alternatively, the assistive channel opening 340 can be positioned at any desired radial position on the catheter body 312.

Similar to catheter body 112 described above, the catheter body 312 can have a proximal section and a distal section. The proximal section of the catheter body 312 can be reinforced similar to the proximal section of the catheter body 112 described above, the details of this and other features or characteristics of the catheter body that are the same as or similar to those of the other catheter bodies described herein are omitted herein for efficiency but considered to be included in these embodiments.

In any embodiments, the distal tip comprising a guidewire channel 348 can be designed to be soft or flexible and atraumatic so as to reduce the risk of puncture and/or injury to the tissue as the catheter body is being advanced through the patient's vessel or passageway. The guidewire lumen 346 can extend through a guidewire channel 348 that can extend distally away from the catheter body 312. The assistive channel inlet is optimally positioned to pass through a side of the catheter body 312 to avoid the guidewire channel 348.

Similar to the aspiration opening 130, the aspiration opening 330 can have a curved profile of an arcuate, parabolic, or other geometry. The edges can be rounded to improve pushability of the catheter and to reduce trauma to the tissue or other risks. The profile of the aspiration opening can optimize the aspiration capabilities of the catheter body 312. In any other embodiments, the aspiration opening 330 can have a flat, angled or beveled profile, or even a square end profile (except for the guidewire channel 348). The length of the catheter body 312 can be approximately the same as or similar to the length of the catheter body 112, including or excluding the portion of the guidewire channel 348 that extends distally away from the catheter body 312 distal to the aspiration opening 330.

The location of the assistive channel inlet 340 relative to the aspiration opening 330 can have an impact on the effectiveness of the assistive jet element to provide the flow or jet of fluid needed to break down or erode thrombus stuck in the aspiration opening 330. With reference to FIG. 23, in some embodiments, the assistive channel inlet 340 can be positioned such that a distance L5 from a proximal edge of the aspiration opening 330 to the closer edge of the of the assistive channel inlet 340 is approximately 5 mm to approximately 100 mm, or from approximately 20 mm to approximately 60 mm. In the illustrated embodiment, the distance L5 also approximately represents the length of an assistive jet channel 342 and an assistive jet channel lumen 344. For coronary applications, the length of the channel 342 (represented by L5) can be from approximately 30 mm to approximately 50 mm.

It is important that the assistive channel inlet 340 be positioned far enough away from the distal end 314 of the catheter body 312 so to not be clogged or impeded by plaque, thrombus, or other debris or tissue near the lesion, but yet close enough to the distal end 314 of the catheter body 312 so that it can clear the end of the guide catheter. Additionally, a shorter assistive jet channel will present less resistance and have less pressure loss than a longer assistive jet channel.

In any embodiments disclosed herein, the assistive channel inlet 340 can have a diameter or size that approximately matches the diameter or size (which can be defined in terms of area) of the assistive jet channel diameter or size. In any embodiments, the assistive channel inlet 340 can have a diameter or size that is approximately ⅓ (33%) of the diameter of the aspiration lumen 332, or from approximately 10% to approximately 15% for 3 Fr compatible catheter, or from approximately 25% to approximately 45% of the diameter of the aspiration lumen 332. In any embodiments disclosed herein, the aspiration flow inlet 340 can have a round, oblong, ovular, triangular, or any other suitable shape. In any embodiments disclosed herein, the assistive channel inlet 340 can have a diameter or size that is approximately 0.5 mm to approximately 3 mm, or from approximately 1 mm to approximately 2 mm.

In any embodiments disclosed herein, the lumen 344 of the assistive jet channel 342 can have a diameter or cross-sectional size that is approximately 25% of the diameter or cross-sectional size of the aspiration lumen 332, or from approximately 10% to approximately 40% of the diameter or cross-sectional size of the aspiration lumen 332. The lumen 344 of the assistive jet channel 342 can, in some embodiments, have a cross-sectional area that is approximately 0.04 $mm^2$, or from approximately 0.02 $mm^2$ to approximately 0.3 $mm^2$. For example, for a 4.2 Fr In any embodiments, a diameter D7 of the aspiration lumen 332 (see FIG. 22) can be any suitable value for the application and size constraint of a particular application. For example and without limitation, in some embodiments, for a 4.2 Fr guide sheath, the maximum outer diameter of an aspiration catheter body that would function optimally (i.e., draw flow from the surrounding fluid, etc.) with such a guide sheath can be approximately 1.22 mm. A suitable assistive jet channel area for this configuration can be approximately 0.02 $mm^2$, which can have an aspiration lumen having a cross-sectional area of approximately 0.22 $mm^2$. In some embodiments, for a 6 Fr guide sheath, the maximum outer diameter of an aspiration catheter body that would function optimally (i.e., draw flow from the surrounding fluid, etc.) with such a guide sheath is approximately 2.16 mm, which can have an aspiration lumen having a cross-sectional area of approximately 1.48 $mm^2$. A suitable assistive jet channel cross-sectional area for this configuration is approximately 0.16 $mm^2$. In some embodiments, for an 8 Fr guide sheath, the maximum outer diameter of an aspiration catheter body that would function optimally (i.e., draw flow from the surrounding fluid, etc.) with such a guide sheath is approximately 2.82 mm, which can have an aspiration lumen having a cross-sectional area of approximately 2.74 $mm^2$. A suitable assistive channel inlet diameter for this configuration is approximately 0.30 $mm^2$. The foregoing values are merely examples and can vary.

Flow rate is a key consideration for the size of the assistive jet channel or lumen size. The channel should not be too small as the size of the lumen may restrict the flow of the viscous blood, which can have other implications. Additionally, flow that is too slow through the channel lumen can also hinder the effectiveness of the assistive jet element, as the slow flow may be unable to effectively erode and break up the thrombus. Conversely, the channel (and also the aspiration lumen itself) should not be so large as to drain blood too quickly from the patient, which can cause hypothermia. The risk of hypothermia may be increased when a pump system is used for the aspiration, such as the Penumbra™ pump.

In any embodiments, the size or diameter of the inlet opening 340 for the assistive jet channel can the approximately the same as or similar to the diameter or size (which can be defined in terms of area) of the assistive jet channel diameter or size. In any embodiments, the assistive jet element can have a plurality of channels and inlets through the catheter body to provide additional flow or jet pathways toward a thrombus stuck in the aspiration window. Without limitation, the assistive jet channels and inlets can be positioned at approximately 3 o'clock and 9 o'clock, or approximately 3 o'clock, 6 o'clock, and 9 o'clock.

Proximal to the assistive jet channel, the aspiration lumen can occupy a larger cross-sectional area than the distal section. In any catheter embodiments disclosed herein, the walls of the catheter body can have a thickness of from approximately 0.003 in to approximately 0.005 in. For example and without limitation, interior walls can have a thickness of approximately 0.003 in, and the exterior walls can have a thickness of approximately 0.005 in. The exterior wall thickness adjacent to the assistive jet channel can be approximately 0.003 in.

Further, any embodiments can have one or more radiopaque bands or markers (not illustrated) near the aspiration opening 330 or assistive channel inlet 340, so that a physician can identify the location of these features under fluoroscopy. Alternatively or in combination with such bands or markers, certain portions of the catheter 310 can comprise a radiopaque material to improve the visibility of such portions under fluoroscopy.

In any embodiments, a length of the guidewire channel 348 can be approximately 15 cm, or can be from approximately 10 cm to approximately 15 cm, or from approximately 5 cm to approximately 15 cm. A diameter D5 of the guidewire lumen can be approximately 0.016 in for a system using 0.014 in guidewire. The diameter D5 of the guidewire lumen in larger systems, such as systems having catheters greater than 14 Fr that are configured to use a 0.018 in guidewire can be approximately 0.020 in. The diameter D5 of the guidewire lumen in systems having catheters greater than 18 Fr that are configured to use a 0.035 in guidewire can be approximately 0.037 in.

Figure 24:
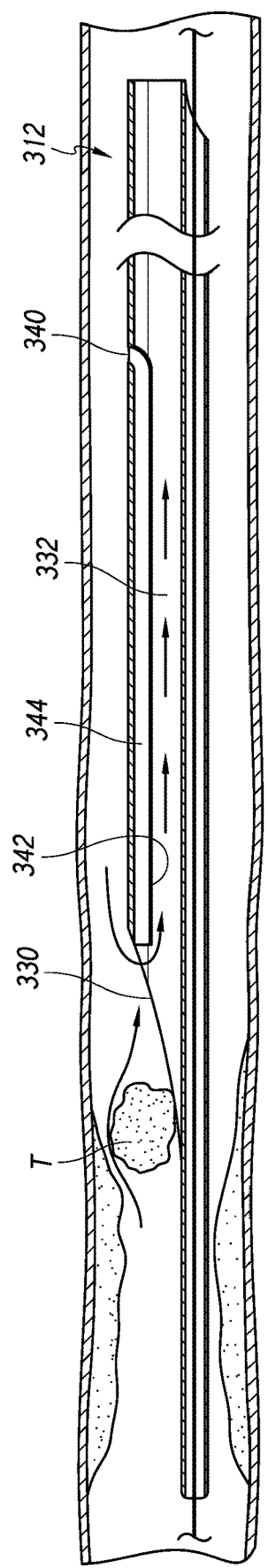
FIG. 24 is a section view of the assistive jet catheter body shown in FIG. 10, illustrating aspiration of thrombus.

FIG. 24 is a section view of the assistive jet catheter body 312, illustrating aspiration of a mass of thrombus T that is located distal to or upstream of the aspiration opening 330 of the assistive jet catheter 310. Because the flow of fluid through the aspiration opening 330 is not impeded by thrombus or otherwise, the flow of blood (indicated by the flow arrows in FIG. 16) through the assistive channel inlet 340 is significantly diminished such that all or most of the flow through the aspiration lumen 332 will go through the aspiration opening 330.

Figure 25:
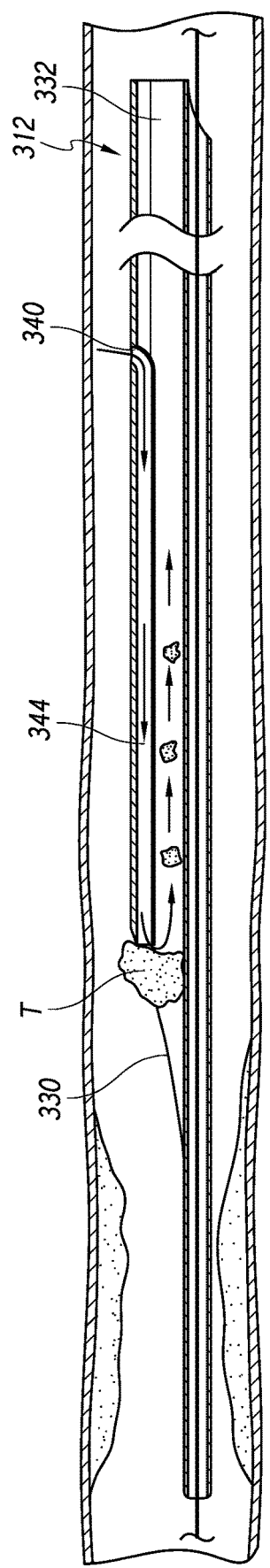
FIG. 25 is a section view of the assistive jet catheter body shown in FIG. 10, illustrating aspiration of thrombus.

FIG. 25 is a section view of the assistive jet catheter body 312, illustrating aspiration of a mass of thrombus T that is located in contact with the aspiration opening 330 of the assistive jet catheter body 312 such that the thrombus T is blocking all or most of the flow through the aspiration opening 330. In this state, because the flow of fluid through the aspiration opening 330 is substantially diminished or is zero, fluid or blood can be drawn through the assistive channel inlet 340, flow through the assistive jet channel 342, out an assistive jet outlet 345, and be directed at the thrombus. Such flow through the channel 342 can be aspirated by the aspiration lumen 332. The assistive channel inlet 340 can be sized and positioned to optimally direct or exert the flow through the assistive jet inlet toward or against the thrombus, so as to break apart or erode the thrombus T. The jet or flow of blood through the assistive channel inlet 340 can eventually break down the thrombus T to a small enough size such that the thrombus T can be aspirated through the aspiration lumen 332, thereby once again reactivating flow through the aspiration opening 330.

Any embodiments disclosed herein can have multiple assistive flow channels supported by or integrally formed with the aspiration lumen. Where there are multiple assistive jet channels, the channels can be radially arranged about the aspiration lumen. Embodiments having multiple assistive jet channels can increase the effectiveness and efficiency of break up and removal of thrombus via aspiration. Embodiments having multiple assistive jet channels can be more effective in clearing thrombus than conventionally available aspiration catheters. Having multiple assistive jet elements (which can comprise assistive jet channels or just assistive jet openings) can have a synergistic effect on the breakdown and removal of thrombus. Multiple assistive jet streams can work together to break down the thrombus at the aspiration opening very efficiently.

In embodiments having multiple assistive jet channels, the inlets can be lined up at the same axial point or region, or can be staggered along the length of the catheter. With aspiration usually done with the aspiration catheter tip at 5 cm to 15 cm deep into the coronary arteries (past the distal end of the guide catheter), the assistive jet inlet holes can be positioned within 5 cm from the tip to increase the likelihood that the holes are exposed to blood to feed the flow and not hidden inside the guide catheter. This design can also be executed as a telescopic assistive jet stream design as described herein and can, therefore, have any of the features, components, or other details of the telescopic assistive jet catheter system of any of the embodiments disclosed herein in combination with any other features disclosed herein. Impeding the flow can occur if the clearance between an inside surface of the guide catheter and an outside surface of the catheter body is too small, e.g., less than approximately 0.003 in. Additionally, the inlet hole may also be pressing against the wall of the guide catheter and impede or prevent flow through the assistive jet channel if the inlet opening is located on a bend in the catheter (which can cause the guide catheter and catheter body to press together).

Alternatively, in some embodiments having assistive jet channels, the inlet opening positioned over a greater distance or range of the catheter body as compared to the through hole assistive jet design because the channel will always have an outflow point dictated by the position of the end of the channel and not the position of the inlet of the channel. In such arrangements, the inlet opening for the channel can be positioned significantly further away from the aspiration window as compared to the through hole assistive jet design, and can be positioned on a portion of the aspiration catheter that is inside the guide catheter, if the clearance between guide catheter and the assistive jet aspiration catheter is greater than a threshold amount. For example and without limitation, a threshold amount can be above approximately 0.003 in, in some embodiments.

Additionally, any embodiments or variations of the assistive channel aspiration catheter system 300 disclosed herein can be adapted for use as an over-the-wire catheter configuration. In some embodiments, this can be achieved by, without limitation, omitting the guidewire channel and adjusting the cross-section of the catheter body accordingly. This can permit the aspiration lumen and/or the assistive jet channel to have a larger cross-sectional size without increasing the overall size of the catheter body. One embodiment of an over-the-wire assistive jet aspiration catheter having an assistive channel jet is described below.

In any embodiments disclosed herein, the channel outlet can be designed with openings at different angles. For example and without limitation, the outlet opening of the assistive jet channel can have a downward angle of approximately 45° to enhance the shearing of the thrombus in front of it without pushing the thrombus away from the aspiration lumen. Additionally, the outlet opening of the assistive jet channel can have a straight opening. The 45° angle of the outlet opening can help reduce the chance of getting the outlet plugged up by the thrombus. In any embodiments, outlet opening of the assistive jet channel can have a 90° downward angle, which can further minimize the risk of clogging. This outlet opening shape and orientation can be effective when a portion of the thrombus is inside the lumen already. The outlet opening of the assistive jet channel can have a 135° angle or any angle past 90°, which can help to push the thrombus in, but may not have much shearing effect on thrombus positioned adjacent to or in contact with the aspiration opening, as the others above.

Finally, in any embodiments, the outlet can be recessed (approximately 0.5 to 2 mm) from a proximal end of the aspiration opening to reduce the chance of clogging. Recessing the outlet or outlow opening too far can result in overly attenuating the flow velocity and shearing force of the assistive jet relative to the thrombus. FIG. 33 is a section view of another embodiment of an assistive channel aspiration catheter 470 of an over-the-wire configuration having a catheter body 472, and assistive jet channel 474, and an aspiration lumen 476. With reference to FIG. 33, a distal end 477 of the assistive jet channel 474 can be recessed in a proximal direction away from a proximal end of the aspiration window 478 by a distance (represented by L6 in FIG. 33) that can be approximately 2 mm, or from approximately 0.5 mm or less to approximately 3 mm or more, or from approximately 0.5 mm to approximately 1.5 mm, depending on the sizes and details of the features of the assistive jet catheter body 472.

FIG. 34 is a section view of another embodiment of an assistive channel aspiration catheter 480 of a rapid exchange guidewire configuration having a catheter body 482, and assistive jet channel 484, and an aspiration lumen 486. With reference to FIG. 34, a distal end 487 of the assistive jet channel 484 can be recessed in a proximal direction away from a proximal end of an aspiration window 488 by a distance (represented by L7 in FIG. 34) that can be approximately 2 mm, or from approximately 0.5 mm or less to approximately 3 mm or more, or from approximately 0.5 mm to approximately 1.5 mm, depending on the sizes and details of the features of the assistive jet catheter body 482.

FIG. 26 is a perspective view of an embodiment of an assistive channel aspiration catheter 410, being of an over-the-wire configuration. Any embodiments of the aspiration catheter 410 can have any of the other features, components, materials, dimensions, and/or other details of any of the other aspiration catheter embodiments disclosed herein, in combination with or in place of any of the features, components, materials, dimensions, and/or other details disclosed with respect to the embodiments of the aspiration catheter 410 described below to form new embodiments. This includes, without limitation, that the assistive channel aspiration catheter 410 can be configured for use with a rapid exchange guidewire system by adding any of the features or components disclosed herein or suitable for use in a rapid exchange guidewire Similarly, any of the other aspiration catheter embodiments disclosed herein can have any of the features, components, materials, dimensions, and/or other details described herein with respect to the aspiration catheter 410 in combination with or in place of any of the features, components, materials, dimensions, and/or other details disclosed with respect to the embodiment of the other aspiration catheters. Further, the embodiments of the aspiration catheter 410 described herein can be configured to work with any of the aspiration catheter system embodiments described herein and/or components thereof. For efficiency, a description of the components and features that are common between the embodiments of the aspiration catheter 410 and the embodiments of the aspiration catheter 310 and/or other aspiration catheter embodiments disclosed herein, as well as the components that can be used with the embodiments of the aspiration catheter 410, will be omitted.

Figure 30:
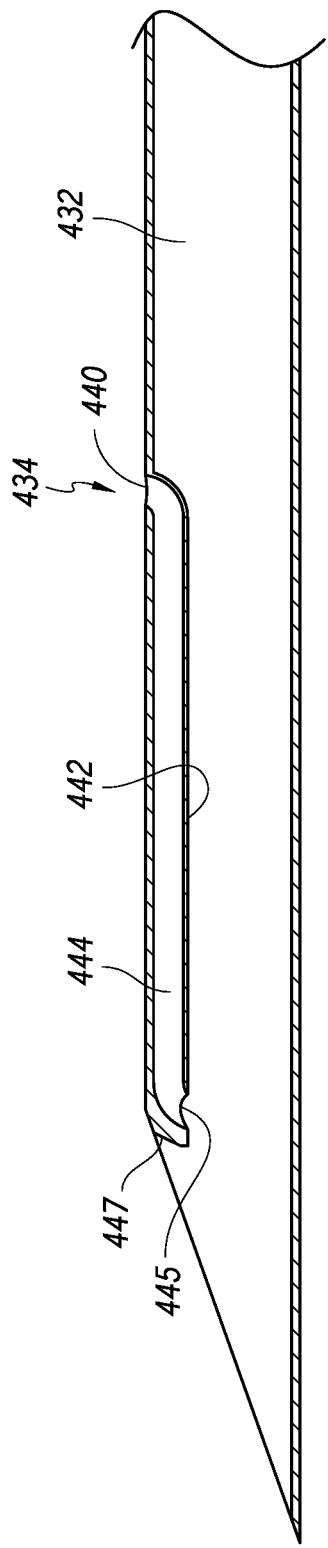
FIG. 30 is a section view of the assistive jet catheter body shown in FIG. 19, taken through line 30-30 of FIG. 28.

FIGS. 27 and 28 are a side view and a top view, respectively, of an assistive channel catheter body 412 shown in FIG. 26. FIG. 29 is a section view of the assistive jet catheter body 412 shown in FIG. 19, taken through line 29-29 of FIG. 27. FIG. 30 is a section view of the assistive jet catheter body shown in FIG. 19, taken through line 30-30 of FIG. 28.

With reference to the figures, in any embodiments, the catheter body 412 can have an aspiration window or opening 430 and an aspiration lumen 432 in communication with the aspiration opening 430 and extending through an entire length of the catheter body 412. Because the assistive catheter embodiment 410 is configured for over-the-wire use, the size of the aspiration lumen 432 extending through the catheter body 412 can be greater than the aspiration lumen 332 of the assistive catheter embodiment 310, which is configured for rapid exchange guidewire procedures. The size of the aspiration lumen 432 can be generally similar to or the same as the aspiration lumen 132 of any of the embodiments of the assistive jet catheters 110 disclosed above, with the exception of the size of the assistive jet channel 442 that is formed in a distal portion of the aspiration lumen 432. Further, in any embodiments, the length, diameter, and other sizes of the assistive jet channels 442 can be generally the same as or similar to any of the assistive jet channels 342 or other assistive jet channels disclosed herein.

The catheter body 412 can also have an assistive jet element 434 configured to direct a flow or jet of fluid (such as blood) into the aspiration lumen adjacent to the aspiration opening, as described herein. The assistive jet element 434 can comprise an assistive channel inlet or channel opening 440 (also referred to herein just as an assistive channel inlet) formed through the catheter body 412 at any desired radial and/or longitudinal location. In the illustrated embodiment, the assistive inlet flow opening can be positioned at a top wall position when the catheter body is in an upright position so that the assistive flow element 434 is closest to a proximal edge of the aspiration opening 430. Alternatively, the assistive channel opening 440 can be positioned at any desired radial position on the catheter body 412.

In any embodiments, the aspiration opening 430 can have a flat but angled profile, a curved profile of an arcuate, parabolic, or other geometry, a square profile, or otherwise.

The edges can be rounded to improve pushability of the catheter and to reduce trauma to the tissue or other risks. The length of the catheter body 412 can be approximately the same as or similar to any other catheter body embodiments disclosed herein, including the embodiments of the catheter body 112.

Figure 31:
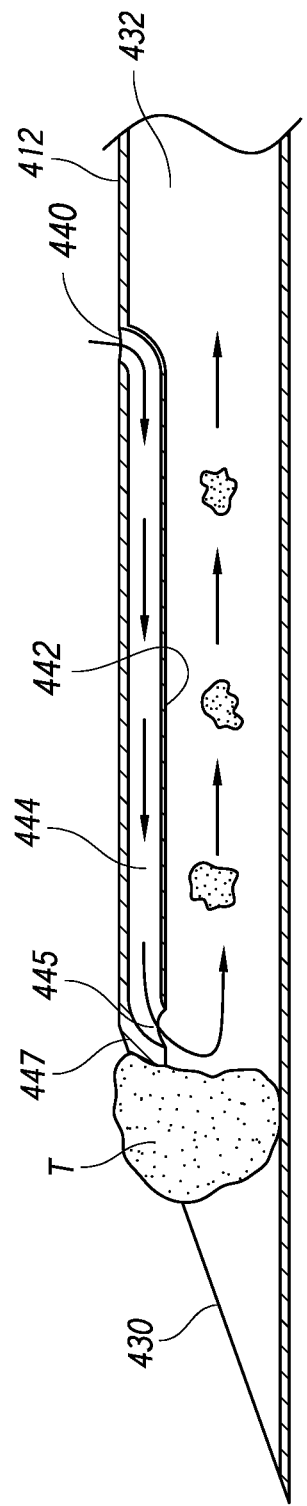
FIG. 31 is an enlargement of the section view of the assistive jet catheter body of FIG. 30, illustrating aspiration of thrombus.

With reference to FIGS. 30 and 31, any embodiments of the assistive jet elements 434 can comprise a deflector or cover element 447 positioned at a distal end of the assistive jet channel 442. The deflector element 447 can block or shield the opening 445 of the assistive channel lumen 444 from blockage or obstruction that may be caused by a thrombus or other debris that may come into contact with the assistive jet channel 442, thereby reducing the likelihood that the opening 445 of the assistive channel lumen 442 will become blocks during aspiration. Additionally, the deflector element 447 can also be configured to direct the jet or flow of fluid flowing through the jet channel lumen 444 in a downward direction. For example without limitation, the deflector element 447 can be configured to direct the jet or flow of fluid flowing through the jet channel lumen 444 at an angle that is approximately 45° relative to the longitudinal axis of the jet channel lumen 444, or from approximately 30° to approximately 60°, or from approximately 15° to approximately 90° or more, relative to the jet channel lumen 444.

FIG. 32 illustrates an embodiment of an aspiration catheter 460 having a catheter body 462 that has an assistive jet channel 464 formed therein, and a deflector element 467 that is configured to direct the jet or flow of fluid flowing through the jet channel lumen 464 at a greater downward direction. For example without limitation, the deflector element 467 can be configured to direct the jet or flow of fluid flowing through the jet channel lumen 464 at an angle that is approximately 90° relative to the longitudinal axis of a jet channel lumen 444, or from approximately 60° to approximately 90° or more, or from approximately 75° to approximately 90°, relative to the jet channel lumen 464.

In the illustrated embodiment, the distal end of the jet channel lumen 444 and the deflector element 447 are positioned adjacent to the proximal most end of the aspiration opening 430. In any other embodiments disclosed herein, all or a portion of the assistive jet channel 442 can be recessed such that the distal end of the jet channel lumen 444 and the deflector element 447 are recessed by from approximately 1 mm to approximately 5 mm within the aspiration lumen 432.

FIG. 31 is a section view of the assistive jet catheter body 412, illustrating aspiration of a mass of thrombus T that is located in contact with the aspiration opening 430 of the assistive jet catheter body 412 such that the thrombus T is blocking all or most of the flow through the aspiration opening 430. In this state, because the flow of fluid through the aspiration opening 430 is substantially diminished or is zero, fluid or blood can be drawn through the assistive channel inlet 440, flow through the lumen 444 of the assistive jet channel 442, the deflector downward by the deflector element 447, and out the assistive jet outlet 445. Such flow through the channel 442 can be aspirated by the aspiration lumen 432. The deflector element 447 can help prevent the lumen 444 of the assistive jet channel 442 from being clogged by the thrombus T. Additionally, imparting the assistive flow or jet at a downward angle can, in some embodiments, optimize the shearing force of the assistive jet on the thrombus T.

FIG. 35 is a side view of another embodiment of an assistive jet aspiration catheter 510, being of an over-the-wire configuration. Any embodiments of the aspiration catheter 510 can have any of the other features, components, materials, dimensions, and/or other details of any of the other aspiration catheter embodiments disclosed herein, in combination with or in place of any of the features, components, materials, dimensions, and/or other details disclosed with respect to the embodiments of the aspiration catheter 510 described below to form new embodiments. Similarly, any of the other aspiration catheter embodiments disclosed herein can have any of the features, components, materials, dimensions, and/or other details described herein with respect to the aspiration catheter 510 in combination with or in place of any of the features, components, materials, dimensions, and/or other details disclosed with respect to the embodiment of the other aspiration catheters. For efficiency, a description of the components and features that are common between the aspiration catheter 510 and the other aspiration catheter embodiments disclosed herein will be omitted.

Further, the embodiments of the aspiration catheter 510 described herein can be configured to work with any of the aspiration catheter system embodiments described herein and/or components thereof. For efficiency, a description of the components and features that are common between the embodiments of the aspiration catheter 510 and the embodiments of the aspiration catheter 310 and/or other aspiration catheter embodiments disclosed herein, as well as the components that can be used with the embodiments of the aspiration catheter 510, will be omitted.

Figure 39:
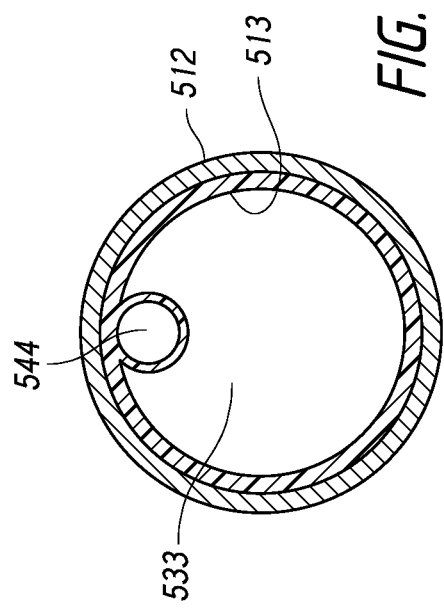
FIG. 39 is a section view of the assistive jet catheter shown in FIG. 35, taken through line 39-39 of FIG. 37.
Figure 40:
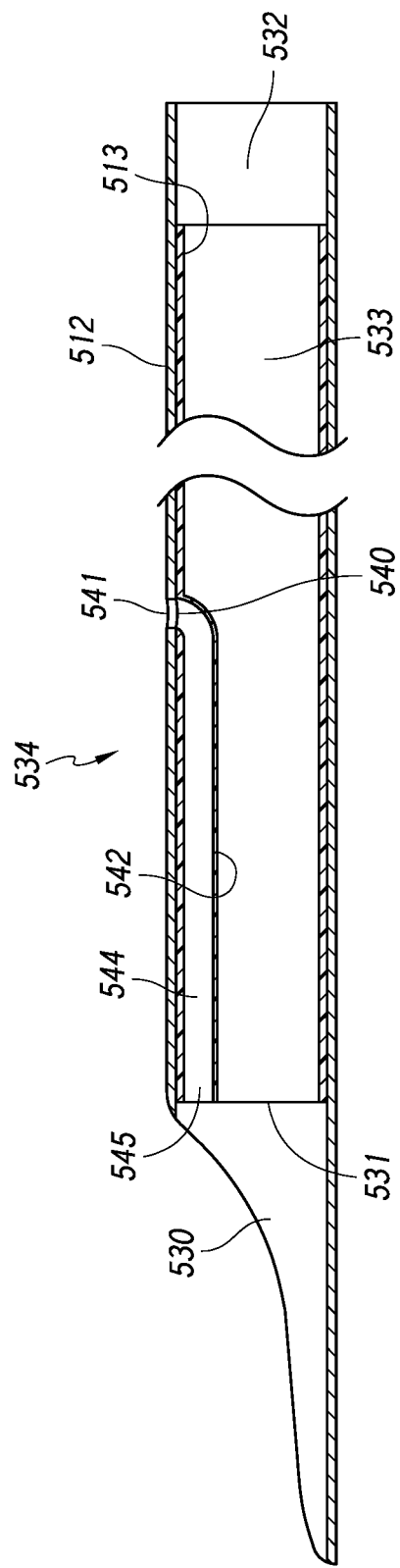
FIG. 40 is a section view of a distal portion of the assistive jet catheter shown in FIG. 35, taken through line 40-40 of FIG. 38.

FIGS. 36, 37, and 38 are a perspective view, a side view, and a top view, respectively, of the assistive jet catheter 510 shown in FIG. 35. FIG. 39 is a section view of the assistive jet catheter 510 shown in FIG. 35, taken through line 39-39 of FIG. 37, and FIG. 40 is a section view of a distal portion of the assistive jet catheter 510 shown in FIG. 35, taken through line 40-40 of FIG. 38.

The assistive jet aspiration catheter 510 (also referred to herein as an assistive jet catheter and just an aspiration catheter) can have a first or outer catheter body 512 having a distal end 514 in a proximal end 516. A first handle 520 can be positioned at a proximal end of the first catheter body 512. The aspiration catheter 510 can also have a second or inner catheter body 513 having a distal end 515 in a proximal end 517. The second catheter body 513 can be configured to slide within the inner diameter of the outer catheter body 512 and can have a second handle 521 at a proximal end thereof. When the aspiration catheter 510 is in an operable position, the proximal end 517 of the inner catheter body 513 will extend proximal of the proximal end 516 of the outer catheter body 512 so that the surgeon can manipulate the inner catheter body 513 relative to the outer catheter body 512 by grasping the second handle 521 coupled with the inner catheter body 513 and the first handle 520 and advancing or withdrawing the handle 521 relative to the first handle 520 and the outer catheter body 512. This relative movement will simultaneously advance or withdraw the inner catheter 513 relative to the outer catheter body 512.

With reference to the figures, in any embodiments, the first or outer catheter body 512 can have an aspiration opening 530 at a distal end thereof and a first aspiration lumen 532 in communication with the aspiration opening 530 and extending through an entire length of the outer catheter body 512. The second or inner catheter body 513 can have an aspiration opening 531 at a distal end thereof and a second aspiration lumen 533 in communication with the aspiration opening 531 and extending through an entire length of the catheter body 513. The length of the outer catheter body 512 can be generally the same as or similar to any of the other catheter body embodiments disclosed herein, while the inner catheter body 513 can be longer than the outer catheter body 512 so that the inner catheter body 513 can extend in a proximal direction beyond the proximal end of the outer catheter body 512.

The first or outer catheter body 512 can be configured to aspirate fluid and thrombus, as well as to slidably receive the second or inner catheter body 513 therethrough. The first and second catheter bodies 512, 513 can be configured to minimize the gap between an outer surface of the inner catheter body 513 and an inner surface of the outer catheter body 512, to maximize space and to limit blood or fluid flow between the inner and outer catheter bodies 512, 513. The inner and outer catheter bodies 512, 513 can be configured such that the gap therebetween is from approximately 0.0015 in to approximately 0.003 in.

In some embodiments, the first and/or second catheter bodies 512, 513 can have indexing features to maintain the catheter bodies in a radial alignment. Additionally, some embodiments of the first and/or second catheter bodies 512, 513 can have stops or other features to limit how far the distal end 515 of the inner catheter body 513 can be advanced relative to the outer catheter body 512. This can facilitate alignment of the first and second catheter bodies 512, 513 in an axial direction when the second catheter body 513 advanced to the point of reaching the stop or axial limit. As will be described, this can facilitate alignment of the openings 540, 541 of an assistive jet element 534.

Figure 41:
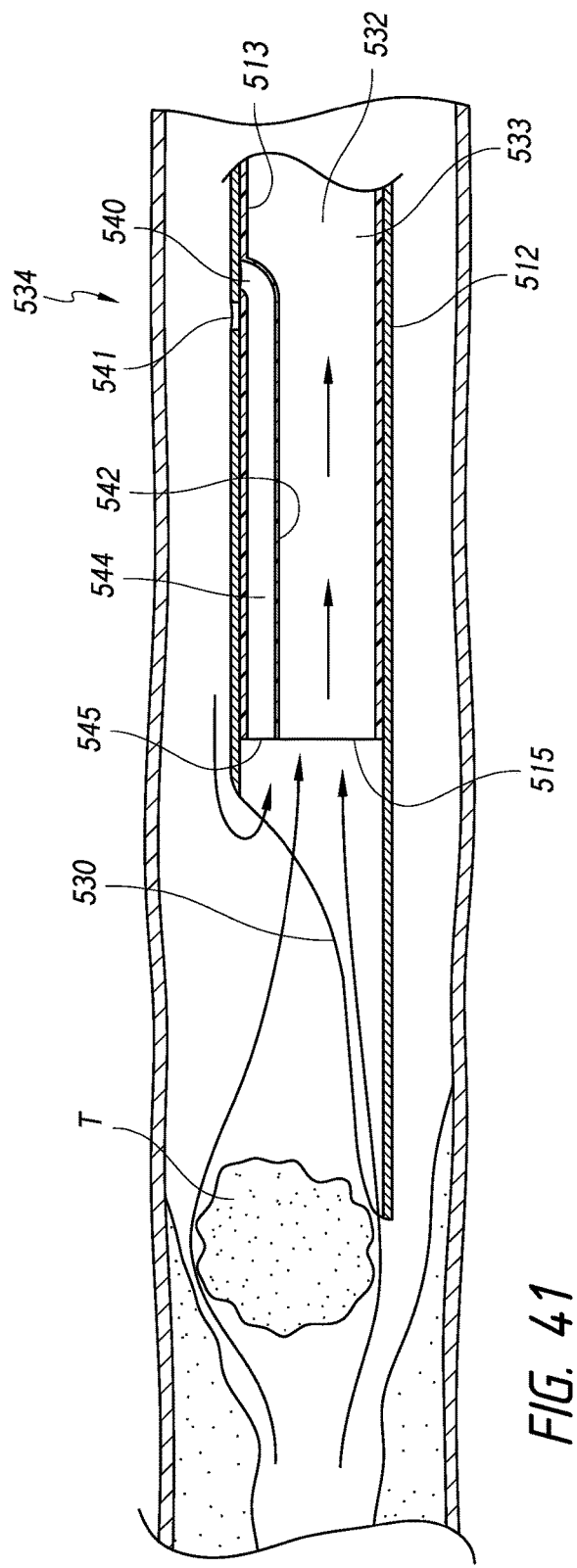
FIG. 41 is a section view of a distal portion of the assistive jet catheter shown in FIG. 35, illustrating aspiration of a mass of thrombus.
Figure 42:
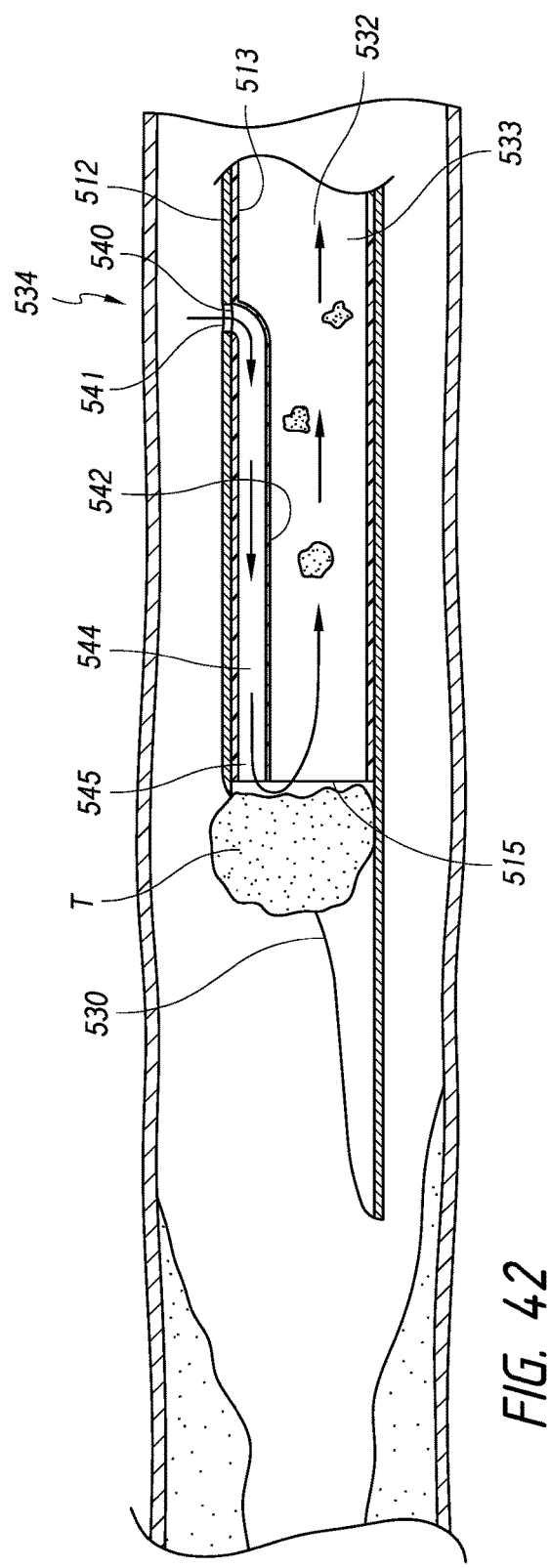
FIG. 42 is a section view of a distal portion of the assistive jet catheter shown in FIG. 35, illustrating aspiration of a mass of thrombus.

In some embodiments, when the inner catheter body 513 is advanced in a distal direction to a first position, wherein the inner catheter body 513 is advanced as far distally as possible relative to the outer catheter body 512, the assistive jet element 534 will be in an open or activated state, which is shown in FIG. 40 and FIG. 42. The assistive jet element 534 can be moved to a closed state, which is shown in FIG. 41, by withdrawing the inner catheter body 513 relative to the outer catheter body 512. Any embodiments of the aspiration catheter 510 can have stops or other features that limit a movement of the inner catheter body 513 relative to the outer catheter body 512 between the first and second positions. In any embodiments, the distance between the first and second positions can be from, for example and without limitation, approximately 5 mm to approximately 10 mm.

With reference to the figures, the assistive jet element 534 can be configured to direct a flow or jet of fluid (such as blood) into the aspiration lumen adjacent to the aspiration opening, as described herein. The assistive jet element 534 can comprise an assistive channel inlet or channel opening 540 (also referred to herein just as an assistive channel inlet) formed through the inner catheter body 513 at any desired radial and/or longitudinal location. Other embodiments having an inner catheter body and an outer catheter body, such as described above, can have an assistive jet element that does not have a channel. In the illustrated embodiment, the assistive inlet flow opening 540 can be positioned at a top wall position when the catheter body 513 is in an upright position so that the assistive flow element 534 is closest to a proximal edge of the aspiration opening 530. Alternatively, the assistive channel opening 540 can be positioned at any desired radial position on the catheter body 513. Additionally, the opening 541 can be formed in the outer catheter body 512 which can align with the opening 540 formed in the inner catheter body 513 when the inner catheter body 513 is in the first position, as shown in FIG. 40 and FIG. 42. In any embodiments, the opening 541 in the outer catheter body 512 can be the same size as or slightly larger (by, for example and without limitation, approximately 10%-20%) than the opening 540 in the inner catheter body 513. The openings 540, 541 can be circular, ovular, oblong, or any desired shape.

In this configuration, the user can selectively activate and deactivate the assistive jet element 534 by advancing the inner catheter body 513 to the first position, so as to activate the assistive jet element 534, and withdrawing or pulling the inner catheter body 513 in a proximal direction relative to the outer catheter body 512 to the second position, or any position where the openings 540, 541 are out of alignment wherein the outer catheter body 512 essentially seals the opening 540, to deactivate the assistive jet element 534. In some embodiments, the aspiration catheter 510 can be configured such that the user activate and deactivate the assistive jet element 534 by rotating the inner catheter body 513 relative to the outer catheter body 512, thereby causing the openings 540, 541 to be out of alignment.

FIG. 41 is a section view of a distal portion of the assistive jet catheter 510 shown in FIG. 35, illustrating aspiration of a mass of thrombus T that is located distal to or upstream of the aspiration opening 530 of the assistive jet catheter 510. The flow of fluid through the aspiration opening 530 is not substantially impeded by thrombus or otherwise. The user has not activated the assistive jet element 534, so little to no blood or fluid is flowing through the assistive jet element 534. All or most of the flow through the aspiration lumen 533 goes through the aspiration opening 530.

FIG. 42 is a section view of a distal portion of the assistive jet catheter 510 shown in FIG. 35, illustrating aspiration of a mass of thrombus T that is located in contact with the aspiration opening 530 of the assistive jet catheter body 512 such that the thrombus T is blocking all or most of the flow through the aspiration opening 530. In this state, the flow of fluid through the aspiration opening 530 is substantially diminished or is zero. As the user applies suction to the catheter 510, when the assistive jet element 534 is activated by advancing the inner catheter body 513 to the first position, fluid or blood can be drawn through the assistive channel inlets 540, 541, flow through the lumen 544 of the assistive jet channel 542, out the assistive jet outlet 545, and be directed at the thrombus. Such flow through the channel 542 can break down the thrombus T and can be aspirated by the aspiration lumen 533 formed in the inner catheter body 513.

The assistive channel inlet 540 can be sized and positioned to optimally direct or exert the flow through the assistive jet inlet toward or against the thrombus, so as to break apart or erode the thrombus T. The jet or flow of blood through the assistive channel inlet 540 can eventually break down the thrombus T to a small enough size such that the thrombus T can be aspirated through the aspiration lumen 533, thereby once again reactivating flow through the aspiration opening 530. Once this is achieved, the user can deactivate the assistive jet element 534 by withdrawing the inner catheter body 513 to the second position. Of course, in any embodiments, deactivation can be achieved by advancing the inner catheter body 513 distally, such that the operation of the catheter body 510 to activate and deactivate the assistive flow element 534 will be opposite or different than as described above.

Any embodiments disclosed herein can have multiple assistive flow channels supported by or integrally formed with the aspiration lumen. Where there are multiple assistive jet channels, the channels can be radially arranged about the aspiration lumen. Embodiments having multiple assistive jet channels can increase the effectiveness and efficiency of break up and removal of thrombus via aspiration. Embodiments having multiple assistive jet channels can be more effective in clearing thrombus than conventionally available aspiration catheters. Having multiple assistive jet elements (which can comprise assistive jet channels or just assistive jet openings) can have a synergistic effect on the breakdown and removal of thrombus. Multiple assistive jet streams can work together to break down the thrombus at the aspiration opening very efficiently.

Additionally, in some embodiments, having multiple assistive jet channels inside of the aspiration lumen can constrict or narrow the flow area of the aspiration lumen, which can create a fluid dynamics advantage called the Venturi effect. The Venturi effect can increase the flow velocity of the blood through the constricted portion of the aspiration lumen to increase the suction force exerted on the thrombus that is broken down at the aspiration opening.

In some embodiments, the aspiration lumen can also have a constricted portion adjacent to the assistive jet opening. The constricted portion of the aspiration lumen can have a cross-sectional area that is approximately 30% less than a cross-sectional area of the unconstricted portion of the aspiration lumen proximal to the constricted portion, or from approximately 35% to approximately 50% less than a cross-sectional area of the unconstricted portion of the aspiration lumen proximal to the constricted portion. Additionally, an entrance profile of the assistive jet opening through the catheter body wall can be angled, so as to direct the assistive jet at an angle relative to the vertical orientation. In the illustrated embodiment, the entrance profile of the assistive jet opening is configured to direct the assistive jet at an angle in a proximal direction relative to the vertical orientation (i.e., toward the proximal end of the catheter body). In other embodiments, not illustrated, the entrance profile of the assistive jet opening can be configured to direct the assistive jet at an angle in a distal direction relative to the vertical orientation (i.e., toward the distal end of the catheter body), or can be configured to direct the assistive jet straight into the aspiration lumen (parallel with the vertical direction).

The constricted portion of the aspiration lumen can cause a substantial increase in the flow velocity of fluid and debris through the constricted portion. The high velocity flow rate can increase a suction force applied to thrombus, and can increase a shear force applied to a thrombus in the aspiration lumen from the assistive jet. In some embodiments, the location and/or size of the assistive jet opening(s) and the size of the constriction can be optimized to provide optimal suction through the constricted portion without excessively reducing the flow through the aspiration lumen. Additionally, the angle and relative positions of the side holes can also be sized and configured to optimize the Venturi effect and also to optimize the shearing effect on the thrombus.

In some embodiments, the constricted portion can be created by a thicker wall portion of the aspiration catheter body. The wall portion adjacent to the constricted portion of the aspiration lumen can be tapered. In some embodiments, the taper can extend further in the distal direction than in a proximal direction. The side hole can be positioned at a leading edge of the constriction.

In any embodiments disclosed herein, the one or more constrictions can have a tapered profile, or a double tapered profile. For example and without limitation, any constriction disclosed herein can have a middle portion, a leading portion that is upstream relative to the flow direction through the aspiration lumen or distal to the middle portion, and a trailing portion that is downstream or proximal to the middle portion and the leading portion. In some embodiments, a length or thickness of the protrusion of the middle portion can be greater than the leading or trailing portion, such that the middle portion projects further into the flow stream within the aspiration lumen than either the leading or trailing portion.

The leading and/or trailing portion of the constriction can have an angled, tapered, or curved shape or profile along a length thereof (the length being along the axial length of the catheter body), or have any other desired shape or profile along the length thereof. Additionally, in any embodiments, the leading portion can have a first shape or profile along the length thereof, and the trailing portion can have a second shape or profile along the length there, the second shape or profile being different than the first shape or profile. For example and without limitation, a surface of the leading edge can be formed at an angle relative to the outer wall of the catheter body having an orientation of approximately 35 degrees, or from approximately 30 degrees to approximately 40 degrees, or from approximately 20 degrees or less to approximately 45 degrees or more. Additionally, a surface of the trailing edge can be formed at an angle relative to the outer wall of the catheter body having an orientation of approximately 25 degrees, or from approximately 20 degrees to approximately 30 degrees, or from approximately 15 degrees or less to approximately 35 degrees or more. In any embodiments, an angular orientation or pitch of the leading portion can be greater than an angular orientation or pitch of the trailing portion. The length of each portion can vary such that the length of the leading portion and the trailing portion can be different.

Further, in any assistive jet aspiration catheter embodiments disclosed herein, the assistive jet aspiration catheter can have one or more constrictions that are asymmetrically positioned or formed in the aspiration lumen. For example and without limitation, any assistive jet aspiration catheter embodiments can have a protrusion formed on one side of the aspiration lumen, or one both of two sides of an aspiration lumen, with the assistive jet openings formed on one or both of a leading edge of the constrictions. In any embodiments disclosed herein, the constrictions formed on the aspiration lumen can be radially symmetrical or uniform about the inner circumference of the aspiration lumen or can be positioned on only a portion or multiple separate and discrete portions of the circumference of the inner surface of the aspiration lumen.

In any embodiments, the assistive jet element can be monolithically formed with all or a portion of the other features of the catheter body, or can be separately formed and coupled with the other components or features of the catheter body. Any catheter body embodiments can have a proximal portion or section (closer to the user) and a distal portion or section (further away from the user). In any catheter body embodiments disclosed herein, the distal portion can comprise any suitable material, including a polymer such as thermoplastic polyurethane, Pebax, nylon, polyester, polyethylene, polycarbonate, polytetrafluoroethylene, or any other suitable extrudable thermoplastic material. Where multiple lumen or channels are needed, such portions of the catheter can be made using a multi-lumen extrusion tube. Additionally, in any embodiments, the proximal portion can comprise a braid or coil reinforced polymer laminated tube. For small catheters, the braid thickness can be approximately 0.0007 inch. For a 6 Fr catheter, the braid or coil can have a thickness of approximately 0.001 in. For larger catheters, the braid or coil can have a thickness of approximately 0.002 in or less. In any embodiments, the braid or coil reinforcement can extend all the way to the proximal portion, or even up to a point that is just proximal of the inlet opening of the assistive jet element.

Any of the components of any of the embodiments disclosed herein can be made from any materials commonly used for aspiration catheters, or which are suitable for the construction of aspiration catheters. Additionally, in any embodiments disclosed herein, the lumen or channels of the catheter can be coated to reduce or eliminate blood cell adhesion in the flow channel, or to improve the flow rate of blood, thrombus, and other debris or objects through the flow channel.

Any components of any of the embodiments disclosed herein can be made from any suitable materials. Such materials can include thermoplastic polymers, including but not limited to nylon, polyurethane, Pebax, HDPE, PE, polyolefin and the like, and/or metal alloys such as stainless steel, Nitinol, and others. Stainless steel metal wire can be used for reinforcement. The wire can be fabricated into a braid mesh or coil embedded within the polymer layer to provide stiffness, flexibility and kink resistance properties. Braid can use approximately 0.001 in, approximately 0.0015 in, or approximately 0.002 in wires formed into a mesh using a PIC count of from approximately 15 to approximately 30. Alternatively, such wires can be formed into coils at the distal section where the assistive jet channel is located. Then, the wire coils can transition into wire braiding with or without an overlap of 1 to 2 mm proximal to the assistive jet channel. With the limited wall space at the assistive jet channel section of the catheter at the distal end, the use of wire coil can give better flexibility and conserve more space for the aspiration lumen and assistive jet flow channel in this distal end. Similarly and alternatively, polymer fiber such as Radel™, Dacron™, and Kevlar™ can also be used for reinforcement.

The catheter embodiments disclosed herein can be sized to suit the needs of any particular applications, including neurological procedures, vascular procedures, aortic procedures, coronary procedures, peripheral procedures of any kind, and otherwise. For example, for neurological procedures, the approximate outer diameters of the embodiments of the aspiration catheters disclosed herein that can be used for a 4 Fr guide catheter, a 5 Fr guide catheter, and a 6 Fr guide catheter are 1.22 mm, 1.42 mm, and 1.75 mm, respectively, though it may be possible to use slightly larger or slightly smaller aspiration catheters than these. For coronary procedures, the approximate outer diameters of the embodiments of the aspiration catheters disclosed herein that can be used for a 4 Fr guide catheter, a 5 Fr guide catheter, a 6 Fr guide catheter, a 7 Fr guide catheter, and an 8 Fr guide catheter are 1.22 mm, 1.42 mm, 1.75 mm, 2.01 mm, and 2.24 mm, respectively, though it may be possible to use slightly larger or slightly smaller aspiration catheters than these. For vascular procedures, the approximate outer diameters of the embodiments of the aspiration catheters disclosed herein that can be used for a 6 Fr guide catheter, a 7 Fr guide catheter, an 8 Fr guide catheter, a 9 Fr guide catheter, and a 10 Fr guide catheter are 1.75 mm, 2.01 mm, 2.24 mm, 2.44 mm, 2.73 mm, respectively, though it may be possible to use slightly larger or slightly smaller aspiration catheters than these. For aortic procedures, the approximate outer diameter of the embodiments of the aspiration catheters disclosed herein that can be used for a 14 Fr guide catheter is 4.39 mm, though it may be possible to use a slightly larger or slightly smaller aspiration catheter than this. For peripheral procedures, the approximate outer diameters of the embodiments of the aspiration catheters disclosed herein that can be used for a 3 Fr sheath, a 5 Fr sheath, 6 Fr sheath, a 7 Fr sheath, an 8 Fr sheath, a 9 Fr sheath, and a 10 Fr sheath are 0.91 mm, 1.88 mm, 2.16 mm, 2.49 mm, 2.82 mm, 2.44 mm, and 2.74 mm, respectively, though it may be possible to use slightly larger or slightly smaller aspiration catheters than these.

Any embodiments can have a distal tip, which can be made from a polyurethane polymer or nylon polymer with or without tungsten loaded resin. The tip can comprise a tungsten loaded resin to provide a signal to the user under x-ray of the location of the tip. In some embodiments, the proximal shaft can use a Grilamid L25 to provide a stiff end for pushing. A middle section of the catheter body can transition to Pebax 72D, Pebax 70D, Pebax 63D, Pebax 55D and have Pebax 40D and 35D for the distal end soft section, which can comprise about 10-15 cm of the distal end. If the catheter is used for other areas such as lower limb vasculature, stiffer polymers instead of 40D or 35D Pebax can be used to achieve a stiffer distal end. Thermoplastic polymers, nylon, polyurethane, Pebax, HDPE, PE, polyolefin and the like can be used. But this can be done in metal tube with the configuration will work too.

Any of the aspiration catheter embodiments disclosed herein can be used in the coronary applications as part of the percutaneous coronary intervention (PCI) procedure for STEMI patients and for any other aspiration procedures. Currently, using conventional aspiration catheters, a procedure to remove thrombus in the coronary heart attack situation will typically require a few minutes. With any of the embodiments disclosed herein, it is expected that the amount of time needed to aspirate thrombus in the coronary heart attack situation will be shorter, which can have significant health and safety benefits to the patient.

When aspiration procedures are performed, an introducer or a guide sheath is typically used to guide the catheter embodiments disclosed herein to the desired location. Because a guide sheath may block any inlet openings in the assistive jet elements disclosed herein, the aspiration catheter should be advanced past the distal end of the guide sheath far enough such that the one or more in the openings of the assistive jet elements are positioned distal of the distal end of the guide sheath. Because a guide sheath is used in many procedures, the size of the aspiration catheter may be limited by the inner diameter of the guide sheath, wherein the size of the aspiration catheter may be chosen to ensure proper clearance and fit within the guide sheath.

Any of the aspiration catheter embodiments disclosed herein can be configured to be either an over-the-wire configuration, or a rapid exchange configuration, or any other suitable configuration. With an over-the-wire configuration, after a guidewire has been advanced into the patient's vasculature or vessels, the catheter can be advanced over the guidewire by passing the proximal end of the guidewire, outside of the patient's body, through the aspiration lumen of the catheter body. The guidewire can then be directed out a side port so as to not interfere with the suction source. For the rapid exchange catheter configurations disclosed herein, the catheters can be advanced over the guidewire by passing the guidewire through the guidewire lumen in the rapid exchange catheter. For a comparable outer diameter of the catheter body, the over-the-wire configuration can have a larger aspiration lumen compared to a similar rapid exchange configuration of the aspiration catheter embodiments disclosed herein. Note that, in any embodiments disclosed herein, the guidewire can be withdrawn partially or completely before aspiration procedures have begun so that the guidewire does not interfere with the aspiration.

Figure 43:
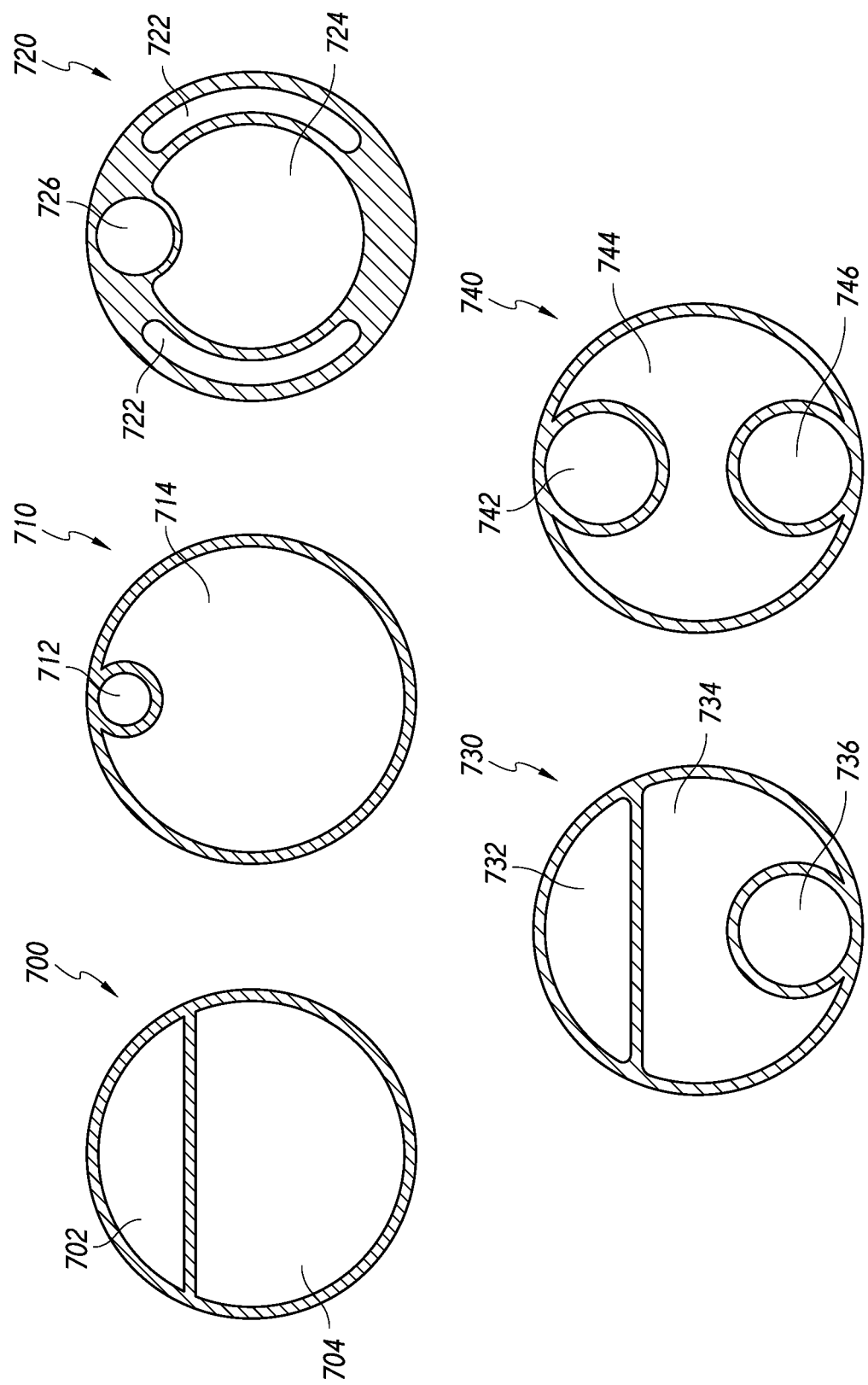
FIG. 43 illustrates a variety of different catheter body cross-sectional configurations that can be used with any of the assistive jet aspiration catheter systems disclosed herein.

FIG. 43 illustrates a variety of different catheter body cross-sectional configurations that can be used with any of the assistive jet aspiration catheter systems disclosed herein. The embodiment of a catheter body 700 illustrated therein can be configured for over-the-wire use, or can be modified for rapid exchange guidewire use. The catheter body 700 can have an assistive jet lumen 702 and an aspiration lumen 704. The assistive jet lumen 702 can have a semicircular shape and can comprise approximately 20%, or from approximately 10% to approximately 30% or more, of the cross-sectional area of the catheter body 700.

The embodiment of the catheter body 710 illustrated therein can be configured for over-the-wire use, or can be modified for rapid exchange guidewire use. Catheter body 710 can have an assistive jet lumen 712 and an aspiration lumen 714. The assistive jet lumen 712 can have a circular shape and can comprise approximately 10%, or from approximately 5% to approximately 20% or more, of the cross-sectional area of the catheter body 710.

The embodiment of the catheter body 720 illustrated therein has been designed to be usable for over-the-wire use, or for rapid exchange guidewire use. Catheter body 720 can have one or more assistive jet lumens 722, each having a curved, oblong shape and an aspiration lumen 724, and a guidewire lumen 726. The assistive jet lumens 722 can, collectively, comprise approximately 10%, or from approximately 5% to approximately 20% or more, of the cross-sectional area of the catheter body 720.

The embodiment of a catheter body 730 illustrated therein can have any of the same properties or features as the catheter body 710, and is configured for rapid exchange guidewire use. The catheter body 730 can have an assistive jet lumen 732, an aspiration lumen 734, and a guidewire lumen 736. The assistive jet lumen 732 can have a semicircular shape and can comprise approximately 20%, or from approximately 10% to approximately 30% or more, of the cross-sectional area of the catheter body 730.

The embodiment of a catheter body 740 illustrated therein can have any of the same properties or features as the catheter body 730, and is configured for rapid exchange guidewire use. The catheter body 740 can have an assistive jet lumen 742, an aspiration lumen 744, and a guidewire lumen 746. The assistive jet lumen 742 can have a circular shape and can comprise approximately 10%, or from approximately 5% to approximately 20% or more, of the cross-sectional area of the catheter body 740.

Any of the catheter embodiments disclosed herein can be used in many parts of the anatomy with early stage thrombus like substances. The catheter embodiments disclosed herein may be suitable for any vessels that are slightly larger (such as a few millimeters larger) than the outer diameter of the catheter body. For example, coronary arteries are mostly from approximately 2 mm to approximately 6 mm, while an aspiration catheter having an outer diameter of approximately 1.73 mm could be used, which would provide a space between the outside of the catheter body and the inside of the vessel wall of approximately 0.27 mm to approximately 4.27 mm for blood to flow to provide the necessary fluid for the assistive jet elements of the embodiments disclosed herein. Similarly, in Above-the-Knee cases, vessels typically have an inside diameter of approximately 7 mm to 8 mm, while the catheters that are typically used have an outside diameter of approximately 1.4 mm, leaving a space of approximately 5.6 mm for the blood flow. The inner diameter or size of neurovascular vessels accessed by catheter are typically about 2 mm to 3 mm, while catheters used for such vessels are usually about 1 mm.

The following is a non-limiting example of a procedure that any of the aspiration catheter embodiments disclosed herein can be used for. A 6F aspiration catheter can be used for this application. The aspiration catheter can be loaded on a 0.014" guidewire, then slowly inserted into the guiding catheter. The physician can have the guiding catheter inserted at a radial (either left or right, though mostly right) entry point or at the common femoral location using an introducer sheath of compatible size. The aspiration catheter can have markings on the proximal shaft to let physician know the tip reaches the tip of the guiding catheter. The catheter can also be connected to a vacuum syringe at the hub end. With diagnostic imaging or angiogram, lesion location is identified.

A physician or medical practitioner can park the catheter just proximal to the lesion and activate the vacuum syringe connected to the catheter. The aspiration catheter can then be slowly advanced over the wire into the lesion and then slowly retracted out. This motion can be repeated with the catheter over the wire the entire time for a few times or until the thrombus inside the ruptured plaque is removed. The physician may use the aspiration catheter to inject contrast dye to diagnose section beyond the lesion. Upon completion, the physician can keep the guidewire and the guide catheter in place and slowly pull out the aspiration catheter.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Accordingly, the scope of the present disclosure is intended to be defined only by reference to the claims of the utility application. The accompanying claims and their equivalents are intended to cover such forms or modifications as would fall within the scope and spirit of the protection. Furthermore, the features and attributes of the specific embodiments disclosed above may be combined in different ways to form additional embodiments, all of which fall within the scope of the present disclosure. Although the present disclosure provides certain embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims or claims that will be added in the future.

Accordingly, although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future. Finally, as used herein and unless otherwise stated, the term approximately is meant to represent a range of +/−10% of the stated value.

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. An assistive jet aspiration catheter comprising:
a catheter body having a distal end, a proximal end, and an outer wall;
an aspiration lumen extending through the catheter body along an axial length of the catheter body from the distal end of the catheter body to the proximal end of the catheter body;
a distal tip positioned at the distal end of the catheter body, the distal tip having an aspiration opening in communication with the aspiration lumen; and
an assistive jet element comprising:
an assistive jet inlet opening extending through the outer wall in the catheter body, opening onto a surface of the outer wall, and positioned proximal to a proximal end of the aspiration opening;
an assistive jet outlet opening positioned distal to the assistive jet inlet opening and toward the proximal end of the aspiration opening; and
an assistive jet channel positioned inside the aspiration lumen and extending in communication with the assistive jet inlet opening and the assistive jet outlet opening;
wherein:
an entirety of the assistive jet element is adapted to be inserted into a vessel of a patient, and
when the aspiration lumen is partially or fully blocked by a thrombus or other mass in the aspiration lumen distal to the assistive jet outlet opening and when suction is applied to a proximal end of the aspiration lumen, the assistive jet element is adapted to draw a bodily fluid of the patient through the assistive jet inlet opening from a location outside of the aspiration lumen and direct an assistive jet flow of the bodily fluid toward the thrombus or the other mass in the aspiration lumen.

2. The assistive jet aspiration catheter of claim 1, wherein the assistive jet element is sized and adapted to draw less than 20% by volume of a total flow aspirated through the aspiration lumen when the aspiration lumen is not blocked.

3. The assistive jet aspiration catheter of claim 1, wherein the assistive jet outlet opening is positioned between approximately 5 mm distal to the proximal end of the aspiration opening to approximately 10 mm proximal to the proximal end of the aspiration opening.

4. The assistive jet aspiration catheter of claim 1, wherein the aspiration opening is angled in a lengthwise direction of the catheter body.

5. The assistive jet aspiration catheter of claim 1, wherein the assistive jet inlet opening is positioned proximal to the proximal end of the aspiration opening by a distance of between 5 mm and 100 mm.

6. The assistive jet aspiration catheter of claim 1, wherein when the aspiration lumen is partially or fully blocked by the thrombus or the other mass in the aspiration lumen distal to the assistive jet outlet opening and when the suction is applied to the proximal end of the aspiration lumen, the assistive jet element is adapted to draw the bodily fluid from around the outer wall of the catheter body through the assistive jet inlet opening.

* * * * *